United States Patent
Leonard

(10) Patent No.: US 12,102,755 B2
(45) Date of Patent: Oct. 1, 2024

(54) CANNULA-BASED VIBRATING MESH NEBULIZER

(71) Applicant: Vapotherm, Inc., Exeter, NH (US)

(72) Inventor: Scott A. Leonard, Bedford, NH (US)

(73) Assignee: VAPOTHERM, INC., Exeter, NH (US)

( * ) Notice: Subject to any disclaimer, the term of this patent is extended or adjusted under 35 U.S.C. 154(b) by 1318 days.

(21) Appl. No.: 16/428,473

(22) Filed: May 31, 2019

(65) Prior Publication Data

US 2019/0366022 A1 Dec. 5, 2019

Related U.S. Application Data

(60) Provisional application No. 62/832,772, filed on Apr. 11, 2019, provisional application No. 62/678,882, filed on May 31, 2018.

(51) Int. Cl.
*A61M 15/08* (2006.01)
*A61M 11/04* (2006.01)
(Continued)

(52) U.S. Cl.
CPC .......... *A61M 15/085* (2014.02); *A61M 11/04* (2013.01); *A61M 11/042* (2014.02);
(Continued)

(58) Field of Classification Search
CPC .... A61M 11/00; A61M 11/005; A61M 15/00; A61M 15/0085; A61M 15/08–085;
(Continued)

(56) References Cited

U.S. PATENT DOCUMENTS 1,149,010 A 8/1915 Olive
2,485,184 A 10/1949 Seymour et al.
(Continued)

FOREIGN PATENT DOCUMENTS

DE 202013006445 8/2013
EP 1317941 A2 6/2003
(Continued)

OTHER PUBLICATIONS

Doshi et al., "High-Velocity Nasal Insufflation in the Treatment of Respiratory Failure: A Randomized Clinical Trial", Annals of Emergency Medicine, Jul. 2017; 72(1):73-83.
(Continued)

*Primary Examiner* — Rachel T Sippel
(74) *Attorney, Agent, or Firm* — McDermott Will & Emery LLP

(57) ABSTRACT

Systems and methods for providing respiratory therapy are disclosed. One device includes a nasal cannula comprising at least at one nasal prong, tubing and a breathing gas conduit. The nasal prong has a proximal tip and a distal end connected to the breathing gas conduit. The breathing gas conduit has an inlet port, an outlet port, and a walled flow path connecting the inlet and outlet ports, such that the conduit directs the breathing gas from the tubing to the proximal tip of the nasal prong. A nebulizer is secured to the nasal cannula and operable to aerosolize a medicament via a vibrating mesh. The vibrating mesh is secured to the nasal cannula and is positioned adjacent to the breathing gas conduit such that the aerosol is entrained with the breathing gas at proximal tip of the nasal prong.

14 Claims, 14 Drawing Sheets

(51) Int. Cl.
*A61M 16/06* (2006.01)
*A61M 16/10* (2006.01)
*A61M 16/14* (2006.01)

(52) U.S. Cl.
CPC ...... *A61M 16/0666* (2013.01); *A61M 16/109* (2014.02); *A61M 16/14* (2013.01); *A61M 2205/0294* (2013.01); *A61M 2205/3344* (2013.01)

(58) Field of Classification Search
CPC ........... A61M 16/0003; A61M 16/0666–0677; A61M 16/108–109; A61M 16/14–164; A61M 16/18–186; A61M 2205/0294; A61M 2205/3344
See application file for complete search history.

(56) References Cited

U.S. PATENT DOCUMENTS

| | | |
|---|---|---|
| 3,826,255 A | 7/1974 | Havstad et al. |
| 3,864,326 A | 2/1975 | Babington |
| 3,945,378 A | 3/1976 | Paluch |
| 4,028,072 A | 6/1977 | Braun |
| 4,177,945 A | 12/1979 | Schwartz et al. |
| 4,805,609 A | 2/1989 | Roberts et al. |
| 4,819,625 A | 4/1989 | Howe |
| 4,832,012 A | 5/1989 | Raabe et al. |
| 4,911,157 A | 3/1990 | Miller |
| 4,915,105 A | 4/1990 | Lee |
| 4,951,661 A | 8/1990 | Sladek |
| 5,099,833 A | 3/1992 | Michaels |
| 5,226,411 A | 7/1993 | Levine |
| 5,335,656 A | 8/1994 | Bowe et al. |
| 5,461,695 A | 10/1995 | Knoch |
| 5,584,285 A | 12/1996 | Salter et al. |
| 5,630,409 A | 5/1997 | Bono et al. |
| 5,752,511 A | 5/1998 | Simmons et al. |
| 6,328,030 B1 | 12/2001 | Kidwell et al. |
| 6,530,370 B1 | 3/2003 | Heinonen |
| 6,539,937 B1 * | 4/2003 | Haveri .................. B06B 1/0253 128/200.14 |
| 6,769,626 B1 | 8/2004 | Haveri |
| 8,561,607 B2 | 10/2013 | Cortez, Jr. et al. |
| 8,740,808 B2 | 6/2014 | Curti et al. |
| 9,333,317 B2 | 5/2016 | Cortez, Jr. et al. |
| 10,265,494 B2 | 4/2019 | Cortez, Jr. et al. |
| 10,471,227 B1 | 11/2019 | Morris |
| 11,420,002 B2 * | 8/2022 | Evans .................. A61M 15/08 |
| 2002/0053346 A1 | 5/2002 | Curti et al. |
| 2003/0150445 A1 | 8/2003 | Power et al. |
| 2004/0011364 A1 | 1/2004 | Dhuper et al. |
| 2004/0221846 A1 | 11/2004 | Curti et al. |
| 2004/0237178 A1 | 12/2004 | Landeros |
| 2005/0217667 A1 | 10/2005 | Dhuper et al. |
| 2005/0229926 A1 | 10/2005 | Fink et al. |
| 2005/0229927 A1 | 10/2005 | Fink et al. |
| 2005/0229928 A1 | 10/2005 | Ivri et al. |
| 2005/0229929 A1 | 10/2005 | Ivri |
| 2005/0252509 A1 | 11/2005 | Rustad et al. |
| 2006/0078506 A1 | 4/2006 | Niven et al. |
| 2006/0120968 A1 | 6/2006 | Niven et al. |
| 2008/0000470 A1 | 1/2008 | Minocchieri et al. |
| 2009/0241948 A1 | 10/2009 | Clancy et al. |
| 2010/0089395 A1 | 4/2010 | Power et al. |
| 2010/0258114 A1 | 10/2010 | Cortez, Jr. et al. |
| 2010/0282247 A1 | 11/2010 | Kadrichu |
| 2011/0000487 A1 | 1/2011 | Moa et al. |
| 2011/0073116 A1 | 3/2011 | Genger et al. |
| 2011/0271962 A1 | 11/2011 | White et al. |
| 2013/0000641 A1 | 1/2013 | Mazela et al. |
| 2013/0074842 A1 | 3/2013 | Boucher et al. |
| 2013/0255670 A1 | 10/2013 | Ott et al. |
| 2013/0267864 A1 | 10/2013 | Addington |
| 2014/0109899 A1 | 4/2014 | Boucher et al. |
| 2015/0150803 A1 | 6/2015 | Boucher et al. |
| 2015/0352299 A1 | 12/2015 | Cortez |
| 2017/0000965 A1 | 1/2017 | Cortez et al. |
| 2018/0064898 A1 * | 3/2018 | Evans .................. A61M 16/14 |
| 2018/0272079 A1 * | 9/2018 | Porter .................. A61M 11/001 |
| 2019/0038851 A1 * | 2/2019 | Hijlkema .......... A61M 15/0085 |
| 2019/0366016 A1 | 12/2019 | Leonard et al. |
| 2020/0368483 A1 * | 11/2020 | Duffy ................ A61M 16/0883 |

FOREIGN PATENT DOCUMENTS

| | | |
|---|---|---|
| JP | 2003250894 | 9/2003 |
| JP | 2007537833 | 12/2007 |
| RU | 2432190 | 10/2011 |
| WO | WO-1989009565 A1 | 10/1989 |
| WO | WO-2002004054 A1 | 1/2002 |
| WO | WO-2003035141 A2 | 5/2003 |
| WO | WO-2005115520 A1 | 12/2005 |
| WO | WO-2006026237 A1 | 3/2006 |
| WO | WO-2006102345 A1 | 9/2006 |
| WO | WO-2009078805 A1 | 6/2009 |
| WO | WO-2009149336 A2 | 12/2009 |
| WO | WO-2010035251 A2 | 4/2010 |
| WO | WO-2010091259 A2 | 8/2010 |
| WO | WO-2012020004 A1 | 2/2012 |
| WO | WO-2012045051 A1 | 4/2012 |
| WO | WO-2013158967 A1 | 10/2013 |
| WO | WO-2015188179 A1 | 12/2015 |
| WO | WO-2016157103 A1 | 10/2016 |
| WO | WO-2017127420 A1 | 7/2017 |
| WO | WO-2018172561 A1 | 9/2018 |
| WO | WO-2018172562 A1 | 9/2018 |
| WO | WO-2018172563 A1 | 9/2018 |
| WO | WO-2019115802 A1 | 6/2019 |

OTHER PUBLICATIONS

International Search Report and Written Opinion for PCT/US2021/065088 dated Jun. 14, 2022 (27 pages).
Spivey S., et al., "Assessment of High Flow Nasal Cannula Therapy use in the Emergency Department Setting: Observations of Practice Across Four Systems", Respiratory Therapy, vol. 10, No. 1, pp. 30-34 (2015).
International Search Report and Written Opinion for PCT/2013/022692 dated Jul. 29, 2014.
International Search Report and Written Opinion for PCT/2010/023331 dated Oct. 19, 2010.
International Search Report and Written Opinion for PCT/US2015/034663 dated Aug. 20, 2015.
International Search Report and Written Opinion for PCT/US2019/035008 dated Sep. 9, 2019.
International Search Report and Written Opinion for PCT/US2019/034978 dated Dec. 11, 2019.
Supplementary European Search Report for EP13740914.0 dated Jul. 8, 2015.
Spence, et al., «Development of a High-Flow Nasal Cannula and Pharmaceutical Aerosol Combination Device», J Aerosol Med Pulm Drug Deliv. Mar. 2, 20191. doi: 10.1089/jamp.2018.1488. [Epub ahead of print] PMID: 30855199.
Sacci, R., "Air entrainment masks: Jet mixing is how they work; The Bernoulli and Venturi Principles are How They Don't", Respiratory Care 1979, vol. 24, No. 10 (4 pages).
Kacmarek et al., "Egan's Fundamentals of Respiratory Care," Physical Principles of Respiratory Care, Chap. 6, 11th Ed., pp. 123-124 (2017) (5 pages).
Cairo, "Mosby's Respiratory Care Equipment," 9th Ed. pp. 20, 98 (2014) (4 pages).
U.S. Appl. No. 13/749,162 filed on Jan. 24, 2013.
U.S. Appl. No. 15/141,492 filed on Apr. 28, 2016.
U.S. Appl. No. 16/293,329 filed on Mar. 5, 2019.
U.S. Appl. No. 17/884,155 filed on Aug. 9, 2022.
U.S. Appl. No. 14/733,180 filed on Jun. 8, 2015.
U.S. Appl. No. 16/428,633, filed May 31, 2019.

(56) References Cited

OTHER PUBLICATIONS

U.S. Appl. No. 18/107,667 filed on Feb. 9, 2023.
U.S. Appl. No. 17/560,947 filed on Dec. 23, 2021.

* cited by examiner

700

Attach source of breathing gas to cannula — 710

Attach vibrating mesh nebulizer to cannula — 720

Entrain aerosol into flow of breathing gas — 730

FIG. 7

CANNULA-BASED VIBRATING MESH NEBULIZER

CROSS-REFERENCE TO RELATED APPLICATIONS

This application claims priority to U.S. provisional application No. 62/678,882, filed May 31, 2018, and U.S. provisional application No. 62/832,772, filed Apr. 11, 2019, the contents of which are hereby incorporated herein by reference in their entirety.

BACKGROUND

Patients with respiratory ailments may be administered supplemental breathing gases, such as oxygen, for example, to aid in respiration. These breathing gases are typically provided from a source of breathing gas, such as an oxygen tank and delivered through a delivery device, such as a nasal cannula, that is coupled to the source of breathing gas and inserted into a patient's nasal passages for delivery of the breathing gas. Separately, some respiratory medications are administered through inhalation, where the medicament or drug is aerosolized by a nebulizer and delivered to the patient's lungs by inhalation.

But delivering nebulized drug therapy though a nasal cannula poses several significant challenges. One significant problem is rain-out. This occurs when the nebulized particles condense and adhere to a surface of the device such as the inner walls of the delivery device and coalesce into large droplets. Such large droplets are usually too large to be respirable. Further, when nebulized particles are contained in a flow, any change in flow direction or turbulence can cause particles to impact a surface. This is exacerbated by high velocity flows where the change in direction is more abrupt. In such situations, the gas is able to change direction, but the inertia of the particles causes them to move toward the outside of any turn in the nasal cannula and impact the wall of the conduit. The rain-out must therefore be collected and disposed of in some way. If the rain-out is instead sent to the patient, the large drops are clinically ineffective and irritating to the patient.

Additionally, the geometric arrangement of common nasal cannulas can contribute to rainout. This can arise particularly in the case of cannulas having small cross sections and one or more directional changes. Rain-out occurs where the gases flow through the cannula at high velocity but collide with the wall at the directional change areas, leading to droplet formation. In some situations, a high percentage of nebulized drug will rain out, in some cases as high as 75% of the nebulized drug.

In many available systems, nebulization of the drug occurs either near a capital unit located away from the patient (machine proximate nebulization) or near the patient (patient proximate nebulization). Each method of nebulization has their challenges.

In machine proximate nebulization, because the capital unit is located away from the patient, the nebulized particles must travel in the gas flow path along the length of the delivery tube before reaching the patient. The longer the nebulized particles travel along the gas flow path, the greater the chance of rain-out occurring in the delivery tube. Further, as the delivery tube essentially comprises an extended lumen with a proximal end and a distal end, the distal end coupled to a cannula connected to the patient, there is no opportunity to collect rain-out that occurs in the delivery tube or the cannula. This can result in the rain-out being delivered to the patient, which is undesirable.

In patient proximate nebulization, the nebulizer is placed on the patient. Any rain-out that is collected must be transported away from the patient. This may involve either emptying a reservoir regularly or providing a conduit to carry the drug away from the patient.

Nebulized drug therapy can also be implemented by using entrainment to introduce the nebulized particles in the gas flow path. Here, the nebulized drug particles are contained in a conduit separate from that containing the flow of breathing gas. These nebulized drug particles are carried by a low velocity gas flow and combine with the nasal cannula at the prongs of the cannula. The low pressure zone created by the high velocity flow of breathing gas draws the nebulized particles into the flow of breathing gas and carries them to the patient via the prongs of the cannula.

Some nebulizers are cumbersome and often involve a multitude of orientation-specific components, such as a reservoir containing the drug and connected to a section of 22 mm diameter respiratory tubing. Owing to the size, shape and required orientation of such nebulizers, generation of nebulized particles at the entrainment site would require the caregiver or patient to hold the nebulizer in a precise location and orientation for an extended period of time during the course of the treatment.

SUMMARY

Disclosed herein are approaches for addressing various of the problems and shortcomings of the state of the art, as identified above. More particularly, disclosed herein are systems and methods for providing respiratory therapy to a patient. According to a first embodiment of the present disclosure, there is provided a system comprising a nasal cannula and a nebulizer. The nasal cannula comprises at least at one nasal prong, tubing configured to receive breathing gas from a breathing gas source, and a breathing gas conduit disposed between the nasal prong and the tubing. The nasal prong has a proximal tip configured to be positioned within the patient's nare and a distal end connected to the breathing gas conduit. The breathing gas conduit has an inlet port in fluid communication with the tubing, an outlet port in fluid communication with the distal end of the nasal prong, and a walled flow path connecting the inlet and outlet ports, such that, when in use, the conduit directs the breathing gas from the tubing to the proximal tip of the nasal prong. The walled flow path has a luminal interior, a distal exterior surface and a proximal exterior surface, wherein the proximal exterior surface is positioned between the distal exterior surface and the proximal tip of the nasal prong and is configured to be placed adjacent the patient when in use. The nebulizer is secured to the nasal cannula and is adapted to receive and deliver a medicament. Embodiments of the nebulizer use a vibrating mesh operable to aerosolize the medicament wherein the medicament is transformed from a liquid into an aerosol of medicament particles. The nebulizer (e.g., the vibrating mesh) may be secured to the nasal cannula. The nebulizer (e.g., the vibrating mesh) may be positioned adjacent to the breathing gas conduit and configured such that, during aerosolization, the aerosol is entrained with the breathing gas at an entrainment zone located near the exit port of the nasal prong. In this configuration, liquid medicament to be fed directly to the nebulizer at the point of aerosol generation, thus minimizing rain-out that would have occurred in a delivery tube had the aerosolized medicament been generated elsewhere and transported to the nasal cannula. This increases the efficacy of medicament delivery.

In certain implementations, the nasal cannula may comprise two nasal prongs. The vibrating mesh may be positioned between the two nasal prongs. One nasal prong may be shorter than the other nasal prong. In certain implementations, the cannula may comprise an antechamber between the nasal prongs into which the aerosol is provided.

In some implementations, the vibrating mesh may be positioned distal of the proximal tip of the nasal prong. In further implementations, the vibrating mesh may be positioned between the distal exterior surface and the proximal tip of the nasal prong. In certain implementations, the vibrating mesh may be positioned on top of the breathing gas conduit. In some implementations, the vibrating mesh may be positioned axially between the proximal tip of the nasal prong and the distal end of the nasal prong. In further implementations, the vibrating mesh may be positioned at the distal exterior surface of the breathing gas conduit. In certain implementations, the vibrating mesh may be positioned at the proximal exterior surface of the breathing gas conduit. In some implementations, the vibrating mesh may be adjacent to the distal exterior surface of the breathing gas conduit. In the aforementioned configurations, the position of the aerosol generating mesh of the nebulizer is precisely specified in relation to the geometry of the cannula and nasal prongs. Such a configuration ensures that the initial velocity of the aerosol particles is directed towards an entrainment zone at the tip of the nasal prongs such that the medicament can be drawn into the flow of breathing gas emerging from the nasal prongs slipstream.

In certain implementations, the nebulizer may be secured to the nasal cannula with any one of a clamp, a snap-fit connector, and an I-connector. In some implementations, the inlet port and the outlet port of the breathing gas conduit may be contiguous with the nasal cannula tubing. The inlet port of the breathing gas conduit may be formed in the nasal cannula tubing. In certain implementations, the system may further comprise an outlet tube positioned so as to direct the aerosol to the entrainment zone. The outlet tube may be shorter than the nasal prong.

In further implementations, the nebulizer may be contained in a housing that comprises a reservoir for the medicament. In certain implementations, the nebulizer may further comprise a piezoelectric ring that may be connected to the vibrating mesh. The housing may contain the piezoelectric ring. The housing may comprise electrical contacts extending from the piezoelectric ring to an exterior of the housing. The vibrating mesh may be operable to aerosolize the medicament upon receipt of an electric signal at the electrical contacts. In certain implementations, the housing may contain O-rings to achieve a liquid tight seal between the reservoir and the housing.

The housing enables the nebulizer to be releasably attached to the cannula such that the vibrating mesh that secures the position of the mesh relative to the nasal prongs of the cannula. This ensures entrainment of aerosolized medicament generated by the nebulizer with the flow of breathing gas at the prongs. Such an arrangement also ensures that the efficacy of drug delivery is not compromised when the patient moves as the mesh will stay in position in the cannula housing. The cannula may be provided with a housing that attaches to the cannula tubing, onto which the nebulizer can be releasably attached. This eliminates the need for specially designed cannulas with an integral housing, and thus the above effects can be achieved with any cannula known in the art. The nebulizer may also be provided with a flexible attachment cuff that securely couples to the cannula tubing. This would allow the vibrating mesh nebulizer to be attached to a cannula that is already secured to the patient, thereby enabling the implementation of nebulization therapy without having to interrupt the flow of breathing gas being provided to the patient.

In some implementations, the medicament may be supplied from a supply bag to the reservoir via a feed line comprising microbore tubing. In further implementations, the medicament may be supplied to the reservoir under pressure or action of gravity. In certain implementations, the source of breathing gas may be connected to the nasal cannula via a delivery tube.

In some implementations, the electric signal may be transmitted to the nebulizer via a wire. In certain implementations, one or more of the feed line and the wire may be attached to either the nasal cannula or the delivery tube via any one of: bonding, clips, windings and a protective sheath. In further implementations, one or more of the feed line and the wire may be attached to the delivery tube via any one of: bonding, clips, windings and a protective sheath.

In some implementations, the medicament may comprise at least one of: bronchodilators, surfactants and antibiotics. The medicament may comprise at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazoldinone, quinupristin/dalfopristen, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imepinim, and meripenim.

According to a second embodiment of the present disclosure, there is provided a system comprising a nebulizer and a nasal cannula. The nebulizer comprises a vibrating mesh operable to generate an aerosolized medicament. The nasal cannula comprises a nosepiece having at least one nasal prong, the nasal prong having a first end connected to the cannula, and a second end configured to be positioned within the patient's nare, the nasal cannula being in fluid communication with the nosepiece and the nasal prong and configured to provide a flow of breathing gas from a source of breathing gas to the patient via the second end of the nasal prong, the nosepiece having a distal exterior surface and a proximal exterior surface. The nebulizer is operably attached to the nasal cannula such that when the nasal cannula is secured to the patient, the proximal exterior surface of the nosepiece is configured to be adjacent to the patient, and the vibrating mesh is positioned at a nebulizing distance measured from the second end of the nasal prong to the distal exterior surface of the nosepiece. In this configuration, the amount of aerosol coalescing into droplets in the nasal cannula within the nebulizing distance after exiting the vibrating mesh is minimized, thereby enabling the aerosol to be introduced into the flow of breathing gas at an entrainment zone outside the second end of the at least one nasal prong.

In some implementations, the percentage of aerosol that coalesces into droplets is less than any of: about 50%, about 45%, about 40%, about 35%, about 30%, about 25%, about 20%, about 15%, about 10%, about 5%, and about 0%.

In certain implementations, the nasal cannula may comprise two nasal prongs. The vibrating mesh may be positioned between the two nasal prongs. One nasal prong may be shorter than the other nasal prong. In certain implementations, the cannula may comprise an antechamber between the nasal prongs into which the aerosol is provided.

In some implementations, the vibrating mesh may be positioned on top of the breathing gas conduit. In certain implementations, the vibrating mesh may be positioned distal of the proximal tip of the nasal prong. In some implementations, the vibrating mesh may be positioned axially between the proximal tip of the nasal prong and the distal end of the nasal prong. In further implementations, the vibrating mesh may be positioned at the distal exterior surface of the breathing gas conduit. In certain implementations, the vibrating mesh may be positioned at the proximal exterior surface of the breathing gas conduit. In some implementations, the vibrating mesh may be adjacent to the distal exterior surface of the breathing gas conduit. In the aforementioned configurations, the position of the aerosol generating mesh of the nebulizer is precisely specified in relation to the geometry of the cannula and nasal prongs. Such a configuration ensures that the initial velocity of the aerosol particles is directed towards an entrainment zone at the tip of the nasal prongs such that the medicament can be drawn into the flow of breathing gas emerging from the nasal prongs slipstream.

In certain implementations, the nebulizer may be secured to the nasal cannula with any one of a clamp, a snap-fit connector, and an I-connector. In some implementations, the inlet port and the outlet port of the breathing gas conduit may be contiguous with the nasal cannula tubing. The inlet port of the breathing gas conduit may be formed in the nasal cannula tubing. In certain implementations, the system may further comprise an outlet tube positioned so as to direct the aerosol to the entrainment zone. The outlet tube may be shorter than the nasal prong.

In further implementations, the nebulizer may be contained in a housing that comprises a reservoir for the medicament. In certain implementations, the nebulizer may further comprise a piezoelectric ring that may be connected to the vibrating mesh. The housing may contain the piezoelectric ring. The housing may comprise electrical contacts extending from the piezoelectric ring to an exterior of the housing. The vibrating mesh may be operable to aerosolize the medicament upon receipt of an electric signal at the electrical contacts. In certain implementations, the housing may contain O-rings to achieve a liquid tight seal between the reservoir and the housing.

The housing enables the nebulizer to be releasably attached to the cannula such that the vibrating mesh that secures the position of the mesh relative to the nasal prongs of the cannula. This ensures entrainment of aerosolized medicament generated by the nebulizer with the flow of breathing gas at the prongs. Such an arrangement also ensures that the efficacy of drug delivery is not compromised when the patient moves as the mesh will stay in position in the cannula housing. The cannula may be provided with a housing that attaches to the cannula tubing, onto which the nebulizer can be releasably attached. This eliminates the need for specially designed cannulas with an integral housing, and thus the above effects can be achieved with any cannula known in the art. The nebulizer may also be provided with a flexible attachment cuff that securely couples to the cannula tubing. This would allow the vibrating mesh nebulizer to be attached to a cannula that is already secured to the patient, thereby enabling the implementation of nebulization therapy without having to interrupt the flow of breathing gas being provided to the patient.

In some implementations, the medicament may be supplied from a supply bag to the reservoir via a feed line comprising microbore tubing. In further implementations, the medicament may be supplied to the reservoir under pressure or action of gravity. In certain implementations, the source of breathing gas may be connected to the nasal cannula via a delivery tube.

In some implementations, the electric signal may be transmitted to the nebulizer via a wire. In certain implementations, one or more of the feed line and the wire may be attached to either the nasal cannula or the delivery tube via any one of: bonding, clips, windings and a protective sheath. In further implementations, one or more of the feed line and the wire may be attached to the delivery tube via any one of: bonding, clips, windings and a protective sheath.

In some implementations, the medicament may comprise at least one of: bronchodilators, surfactants and antibiotics. The medicament may comprise at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazoldinone, quinupristin/dalfopristen, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imepinim, and meripenim.

According to a third embodiment of the present disclosure, there is provided a method for providing respiratory therapy to a patient. The method comprises attaching a source of breathing gas to a cannula comprising at least one nasal prong, the nasal prong being in fluid connection with the cannula such that a flow of breathing gas from the source of breathing gas is provided to a patient when a proximal tip of the nasal prong is positioned within the patient's nare. The method also comprises attaching a nebulizer to the nasal cannula, the nebulizer having a vibrating mesh secured to the nasal cannula and operable to aerosolize a medicament received by the nebulizer such that the aerosol generated by the vibrating mesh passes into the atmosphere. Further, the method comprises entraining the aerosol into the flow of breathing gas at an entrainment zone located at the proximal tip of the nasal prong. In this configuration, the amount of aerosol coalescing into droplets in the nasal cannula within the nebulizing distance after exiting the vibrating mesh is minimized, thereby enabling the aerosol to be introduced into the flow of breathing gas at an entrainment zone outside the second end of the at least one nasal prong.

In some implementations, the nasal cannula may comprise two nasal prongs such that the vibrating mesh may be positioned between the two nasal prongs. In certain implementations, the cannula may comprise an antechamber between the nasal prongs into which the aerosol is provided. In some implementations, the vibrating mesh may be positioned on top of the nasal prong. In certain implementations, the vibrating mesh may be positioned distal of the proximal tip of the nasal prong. In further implementations, the vibrating mesh may be positioned axially between the proximal tip of the nasal prong and the distal end of the nasal prong. In the aforementioned configurations, the position of the aerosol generating mesh of the nebulizer is precisely specified in relation to the geometry of the cannula and nasal prongs. In some implementations, the method further comprises directing the aerosol to the entrainment zone via an outlet tube. Such a configuration ensures that the initial velocity of the aerosol particles is directed towards an entrainment zone at the tip of the nasal prongs such that the medicament can be drawn into the flow of breathing gas emerging from the nasal prongs slipstream.

In certain implementations, the method further comprises providing an electric signal to the vibrating mesh of the nebulizer via a wire to enable aerosolization of the medicament. In some implementations, the method further comprises supplying the medicament to the nebulizer from a supply bag via a feed line comprising microbore tubing. In further implementations, the method additionally comprises connecting the source of breathing gas to the nasal cannula via a delivery tube. In certain implementations, the method comprises attaching one or more of the feed line and the wire to either the nasal cannula or the delivery tube via any one of: bonding, clips, windings and a protective sheath. In other implementations, the method comprises attaching one or more of the feed line, the wire and the nasal cannula to the delivery tube via any one of: bonding, clips, windings and a protective sheath.

In some implementations, the medicament may comprise at least one of: bronchodilators, surfactants and antibiotics. The medicament may comprise at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazoldinone, quinupristin/dalfopristen, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imepinim, and meripenim.

According to a fourth embodiment of the present disclosure, there is provided nebulizer for generating a flow of aerosolized medicament for delivery to a patient. The nebulizer comprises a chamber having an inlet, an outlet and a pressure port. The nebulizer also comprises a feed tube coupled to the inlet of the chamber for delivery of a liquid medicament from a remote source to the chamber. Further, the nebulizer comprises an aerosol generator coupled to the outlet of the chamber and operable to aerosolize the liquid medicament, the aerosol generator having an inner surface in fluidic contact with the liquid medicament, and an outer surface from which the aerosolized medicament is released for delivery to the patient. Additionally, the nebulizer comprises a pressure adjustment element in communication with the pressure port and configured to regulate the pressure within the chamber such that the pressure at the inner and outer surfaces of the aerosol generator is substantially the same.

In some implementations, the aerosol generator is a vibrating mesh. In certain implementations, the pressure at the inner and outer surfaces of the aerosol generator is maintained at atmospheric pressure. In other implementations, the liquid medicament is drip fed onto the inner surface of the aerosol generator. In some implementations, the liquid medicament is drip fed onto the inner surface of the aerosol generator at atmospheric pressure under the action of gravity. In certain implementations, the inlet connects to a nozzle within the chamber that enables the liquid medicament to be drip fed onto the inner surface of the aerosol generator. In other implementations, the feed tube extends into the chamber and is configured to deliver the liquid medicament directly onto the inner surface of the aerosol generator such that the liquid medicament leaving the feed tube immediately forms a meniscus on the inner surface of the aerosol generator.

In some implementations, the chamber forms a reservoir that is at least partially filled with the liquid medicament such that the liquid medicament is in constant contact with the inner surface of the aerosol generator. In certain implementations, a space develops between the pressure port and the liquid level of the medicament in the chamber. In other implementations, the pressure adjustment element comprises a permeable membrane. In some implementations, the pressure adjustment element additionally comprises a perforated vent. In certain implementations, the permeable membrane comprises a Gore-Tex material. In other implementations, the liquid medicament completely fills the chamber such that the medicament is in contact with the pressure adjustment element and the inner surface of the aerosol generator.

In certain implementations, the pressure adjustment element comprises a compliant diaphragm that is configured to deform in order to regulate the pressure within the chamber. In some implementations, the pressure port and outlet are vertically positioned such that the pressure port is located at a topmost section of the chamber, and the outlet is located at the bottommost section of the chamber. In other implementations, the nebulizer further comprises a piezoelectric ring that is connected to the aerosol generator. In certain implementations, the aerosol generator is operable to aerosolize the liquid medicament upon receipt of an electric signal via electrical contacts connected to the piezoelectric ring. In some implementations, the nebulizer contains O-rings around the outlet to achieve a liquid tight seal between the chamber and the atmosphere. In other implementations, the liquid medicament comprises at least one of: bronchodilators, surfactants and antibiotics.

In some implementations, the medicament comprises at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazoldinone, quinupristin/dalfopristen, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imepinim, and meripenim.

According to a fifth embodiment of the present disclosure, there is provided a system for providing respiratory therapy to a patient. The system comprises a nasal cannula having at least at one nasal prong, tubing configured to receive breathing gas from a breathing gas source, and a breathing gas conduit disposed between the nasal prong and the tubing, the nasal cannula configured to generate a flow of breathing gas from the at least one nasal prong. The system further comprises a nebulizer according to any of the preceding claims, operable to generate a flow of aerosolized medicament. Further, the system comprises a reservoir of liquid medicament located remote from the nebulizer and arranged to supply the nebulizer with the liquid medicament, wherein the nasal cannula is configured to deliver the flow of breathing gas and the flow of aerosolized medicament to the patient for inhalation thereof.

In certain implementations, the nebulizer is coupled to the nasal cannula such that the flow of aerosolized medicament is entrained into the flow of breathing gas within the breathing gas conduit of the nasal cannula and prior to delivery to the patient. In some implementations, the flow of aerosolized medicament is combined with the flow of breathing gas within the breathing gas conduit of the nasal cannula and delivered as a mixed stream to the patient via the nasal prong. In other implementations, the outlet port of the nebulizer is coupled to an opening in the tubing of the nasal cannula. In certain implementations, the outlet port of the nebulizer is in fluid communication with the breathing gas conduit.

In some implementations, the outlet of the nebulizer is coupled to the nasal cannula such that the flow of aerosolized medicament is provided to the patient by entrainment with the flow of breathing gas as the flow of breathing gas exits the at least one nasal prong for inhalation by the patient. In other implementations, the flow of aerosolized medicament is combined with the flow of breathing gas after the flow of breathing gas exits the at least one nasal prong and before inhalation by the patient. In certain implementations, the flow of aerosolized medicament and the flow of breathing gas are maintained as separate flow streams until the breathing gas exits the nasal cannula. In some implementations, the system further comprises a source of breathing gas.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 5A shows an illustrative cross sectional view of the integrated snap-fit cannula based nebulizer of FIG. 5;

FIG. 7 shows a flowchart of an illustrative method of providing cannula based nebulization therapy to a patient;

DETAILED DESCRIPTION

Figure 1:
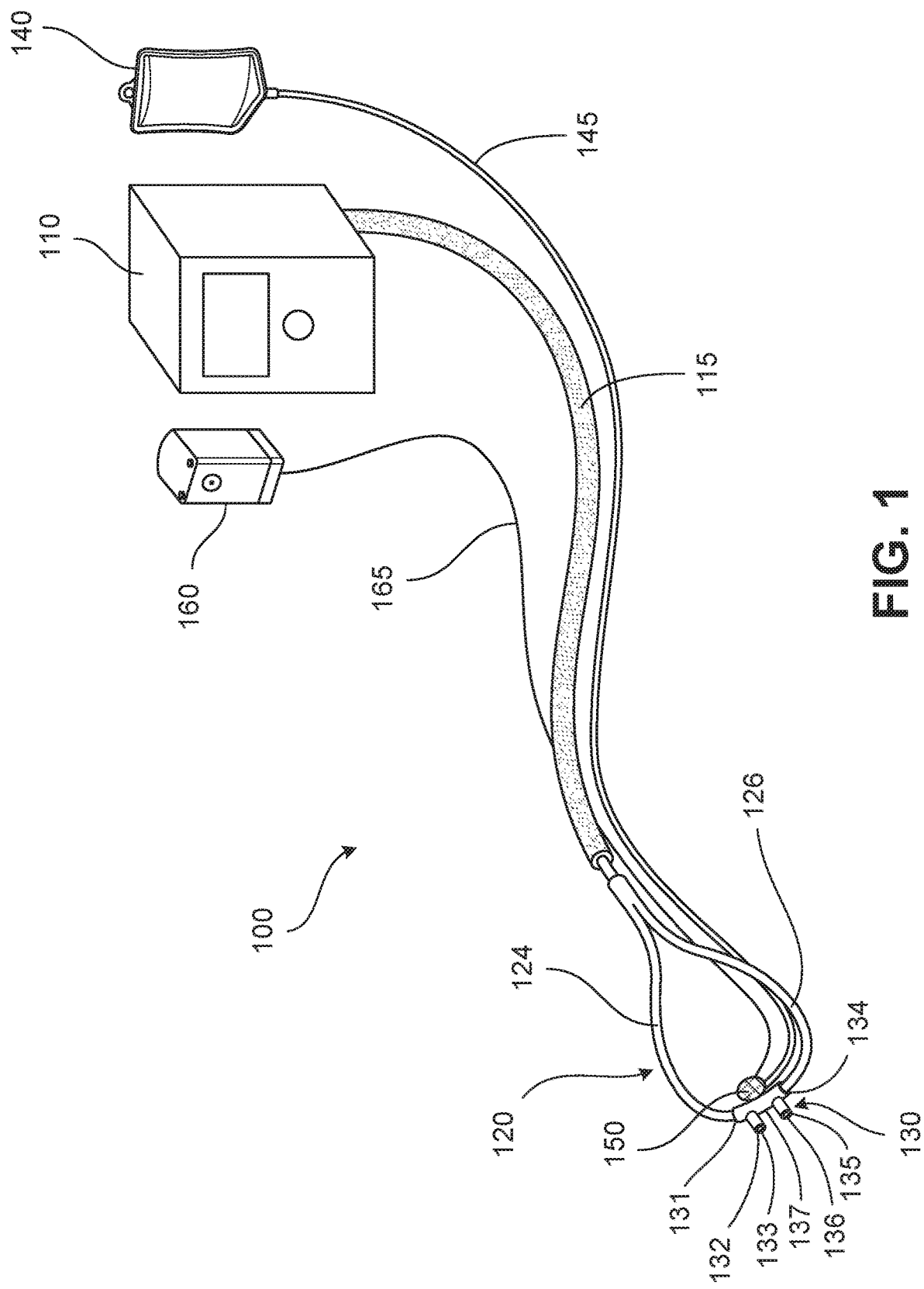
FIG. 1 shows an illustrative cannula based nebulizer according to an embodiment of the present disclosure.

To provide an overall understanding of the systems and methods described herein, certain illustrative implementations will be described. Although the implementations and features described herein are specifically described for use in connection with a high flow therapy system, it will be understood that all the components and other features outlined below may be combined with one another in any suitable manner and may be adapted and applied to other types of respiratory therapy and respiratory therapy devices, including low flow oxygen therapy, continuous positive airway pressure therapy (CPAP), mechanical ventilation, oxygen masks, Venturi masks, and Tracheostomy masks. Furthermore, it should be noted that while certain implementations are discussed herein with regards to systems and methods for respiratory therapy, these various implementations may be used in various combinations to increase both the efficacy of treatment and the patient's overall level of comfort during the treatment.

Disclosed herein are systems and methods that provide respiratory therapy to a patient with a nebulizer secured to a nasal cannula having at least one nasal prong. The nebulizer is described below and generates a stream of aerosolized medicament in close proximity to the nasal prongs of the cannula. The nebulizer is provided with a vibrating mesh that enables liquid medicament to be fed directly to the nebulizer at the point of aerosol generation, thus minimizing rain-out that would have occurred in a delivery tube had the aerosolized medicament been generated elsewhere and transported to the nasal cannula. This increases the efficacy of medicament delivery. The position of the aerosol generating mesh of the nebulizer is precisely specified in relation to the geometry of the cannula and nasal prongs. Such a configuration ensures that the initial velocity of the aerosol particles is directed towards an entrainment zone at the tip of the nasal prongs such that the medicament can be drawn into the flow of breathing gas emerging from the nasal prongs slipstream.

The cannula may include a housing integrally formed in the cannula tubing. The housing enables the nebulizer to be releasably attached to the cannula such that the vibrating mesh that secures the position of the mesh relative to the nasal prongs of the cannula. This ensures entrainment of aerosolized medicament generated by the nebulizer with the flow of breathing gas at the prongs. Such an arrangement also ensures that the efficacy of drug delivery is not compromised when the patient moves as the mesh will stay in position in the cannula housing. The cannula may be provided with a housing that attaches to the cannula tubing, onto which the nebulizer can be releasably attached. This eliminates the need for specially designed cannulas with an integral housing, and thus the above effects can be achieved with any cannula known in the art. The nebulizer may also be provided with a flexible attachment cuff that securely couples to the cannula tubing. This would allow the vibrating mesh nebulizer to be attached to a cannula that is already secured to the patient, thereby enabling the implementation of nebulization therapy without having to interrupt the flow of breathing gas being provided to the patient.

FIG. 1 shows an illustrative system 100 for providing respiratory therapy to a patient. System 100 comprises a capital unit 110 connected to a nasal cannula 120 via a delivery tube 115. In some embodiments of the present disclosure, capital unit 110 may be connected to a source of breathing gas (not shown). Capital unit 110 controls the operation of the nasal cannula 120 by, for example, controlling the flow rate of breathing gas supplied to the nasal cannula 120 from the source of breathing gas. The control unit 110 may additionally heat and humidify the breathing gas before delivering the same to the nasal cannula 120. Such control can be afforded to the capital unit in a multitude of manners that are well known in the art, such as, for example, implementing a control circuit using electronic components, the details of which are omitted from the present disclosure for the sake of brevity.

As shown in FIG. 1, a nebulizer 150 may be coupled to the nasal cannula 120 to provide a stream of aerosolized medicament to the patient. Such medicament is stored in the liquid form in a supply bag 140 located away from the nasal cannula 120. A feed line 145 comprising a microbore tube, for example, may be used to connect the supply bag 140 to the nasal cannula to allow liquid medicament to be fed directly to the nebulizer 150. Nebulizer 150 comprises a vibrating mesh that aerosolizes the liquid medicament from the supply bag 140 upon input of an electrical signal. Such an electrical signal is provided by a signal generator 160 located away from the nasal cannula 120. The electrical signal is transmitted to the nebulizer 150 via a connection cable 165. Once the aerosol is generated by the nebulizer 150, the stream of aerosol is entrained with the flow of breathing gas at the nasal cannula 120 thereby providing respiratory therapy to the patient.

In some embodiments, the feed line 145 and the connection cable 165 may be secured to the delivery tube 115 with clips positioned along the length of the delivery tube 115. In certain embodiments, the connection cable 165 may be wound around the feed line 145 and the delivery tube 115, thereby securing the feed line 145 to the delivery tube 115. In other embodiments, windings may be used to secure the feed line 145 and connection cable 165 to the delivery tube 115. In some embodiments, a protective sheath may be used to house the delivery tube 115, feed line 145 and the connection cable 165. In certain embodiments, the feed line 145 and the connection wire 165 may be secured to the nasal cannula 120 via any of the methods discussed in the foregoing. In certain embodiments, the connection wire 165 may be attached to the delivery tube 115 while the feed line 145 may be attached to the nasal cannula 120.

The source of breathing gas may be configured to provide, for example, breathing gas at flow rates between 1 and 8 liters per minute (lpm) for infants, between 5 and 20 lpm for pediatric patients, or up to 40 lpm for adults. Suitable sources of heated and humidified gas will be known to one of ordinary skill in the art. For example, the source may be the Vapotherm Flowrest System, Vapotherm Careflow System, Precision Flow unit, or the Vapotherm 2000i, all of which are provided by Vapotherm, Inc. of Exeter, New Hampshire, USA. Other suitable sources of breathing gas will be known to one of ordinary skill in the art from the description herein.

The flow of heated and humidified gas from the capital unit 110 is provided to the patient via nasal cannula 120 connected to the delivery tube 115. In some embodiments, nasal cannula 120 may comprise a first tubing 124 having a first lumen therethrough and a second tubing 126 having a second lumen therethrough, as described in U.S. patent application Ser. Nos. 13/665,100, 15/199,158 and 62/555,945, the contents of which are hereby incorporated by reference in their entirety. In certain embodiments, the first and second lumens of the nasal cannula 120 are separate from each other so as to form separate paths for the provision of the flow of breathing gas to the patient. In other embodiments, the first and second lumens of the nasal cannula 120 are connected to each other so as to form a single path for the provision of the flow of breathing gas to the patient.

In some embodiments, delivery tube 115 may have a single lumen connecting the capital unit 110 to the first and second lumens of the nasal cannula 120 for the flow of heated and humidified breathing gas therethrough. In such implementations, the connection between the single lumen delivery tube 115 and the nasal cannula 120 may be facilitated by a flow splitter to ensure division of breathing gas from the capital unit 110 to the first tubing 124 and the second tubing 126 of the nasal cannula 120. In other implementations, delivery tube 120 may comprise a dual lumen tube, where one lumen of the delivery tube 120 is in fluid communication with the first lumen of the first tubing 124 of the nasal cannula 120 and the other lumen of the delivery tube 120 is in fluid communication with the second lumen of the second tubing 126 of the nasal cannula 120.

In some embodiments, the nasal cannula 120 may further comprise a nosepiece 130 having a first nasal prong 133 and a second nasal prong 136. Nosepiece 130 comprises a first inlet 131, a second inlet 134, a first outlet 132 located on the first nasal prong 133 and a second outlet 135 located on the second nasal prong 136, of which the first inlet 131 is in fluid communication with the first outlet 132, and the second inlet 134 is in fluid communication with the second outlet 135. The nosepiece 130 is arranged such that the first lumen of the first tubing 124 of the nasal cannula is in fluid communication with the first inlet 131 and the first outlet 132 of the first nasal prong 133, and the second lumen of the second tubing 126 of the nasal cannula is in fluid communication with the second inlet 134 and the second outlet 135 of the second nasal prong 135. With such a configuration, when the nosepiece 130 is positioned adjacent the upper lip of the patient, the first nasal prong 133 is positioned in a nare of the patient while the second nasal prong 136 is positioned in the other nare of the patient. This allows the heated and humidified breathing gas generated at the capital unit 110 to be provided to the patient. As shown in FIG. 1, nosepiece 130 may comprise a bridge portion 137 between the first and second nasal prongs 133, 135. In some embodiments the bridge 137 may be solid thereby separating the first and second lumens of the cannula 120. In other embodiments, the bridge 137 may comprise a lumen that fluidly connects the first and second lumens of the nasal cannula 120.

While a nasal cannula 120 comprising two nasal prongs 133, 135 has been described in the foregoing, in certain embodiments of the present disclosure the nasal cannula 120 may instead comprise a single nasal prong through which heated and humidified breathing gas is provided to a patient. Exemplary nasal cannulas include the high flow adult cannula VAPMA1700, the pediatric nasal cannula VAPMP1500, the infant cannula VAPMI1300 and the premature cannula VAPMN1100, all of which are provided by Vapotherm, Inc. of Exeter, New Hampshire, USA.

In some embodiments, nasal cannula 120 may be fabricated in a material comprising polyvinyl chloride (PVC) plastic, plastisol, vinyl, silicone, non-latex rubber, an elastomer, ethylene vinyl acetate (EVA), styrene-butadiene copolymer (SBC), polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, a material less than 70 Durometer Shore A, or any other suitable material).

Figure 1A:
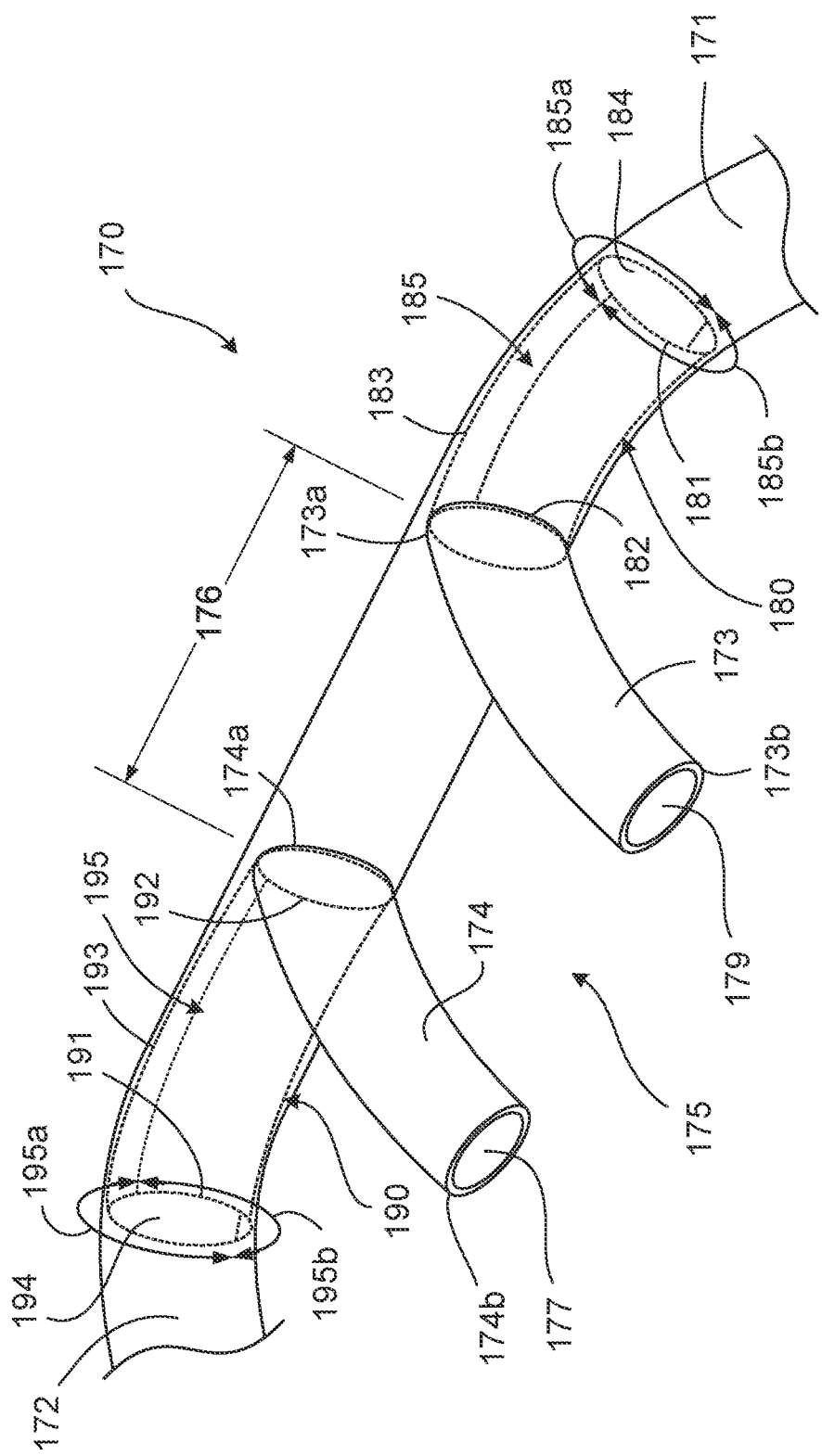
FIG. 1A shows an illustrative nasal cannula according to an embodiment of the present disclosure.

In some embodiments the nasal prongs may be integrally formed in the nasal cannula, as illustrated in FIG. 1A. The nasal cannula 170 in FIG. 1A comprises first tubing 171, second tubing 172, first nasal prong 173, and second nasal prong 174. Although not shown in FIG. 1A, the flow of heated and humidified gas is provided to the cannula 170 via a delivery tube similar to delivery tube 150 shown in FIG. 1. The first tubing 171 has a first lumen and the second tubing 172 has a second lumen, both lumens allowing the flow of heated and humidified gas therethrough. Cannula 170 may comprise a bridge portion 176 between the first and second nasal prongs 173, 174. In some embodiments the bridge portion 176 may be solid thereby separating the first and second lumens of the cannula 170. In other embodiments, the bridge 170 may comprise a lumen that fluidly connects the first and second lumens of the nasal cannula 170. The first nasal prong 173 and the second nasal prong 174 are integrally formed in cannula 170 such that the distal end 173a of the nasal prong 173 is attached to the first tubing 171, and the distal end 174a of the nasal prong 174 is attached to the second tubing 172. A first outlet 179 is located on the proximal tip 173b of the first nasal prong 173 and a second outlet 177 is located on the proximal tip 174b of the second nasal prong 174. The first nasal prong 173, the second nasal prong 174 and the tubing of bridge portion 176 between the nasal prongs 173, 174 form the nosepiece 175, similar to nosepiece 130 shown in FIG. 1.

Nasal cannula 170 comprises a first breathing gas conduit 180, disposed between the distal end 173a of nasal prong 173 and the first tubing 171, and a second breathing gas conduit 190, disposed between the distal end 174a of nasal prong 174 and the second tubing 172. First breathing gas conduit 180 comprises a first inlet port 181 in fluid communication with the first lumen of the first tubing 171, a first outlet port 182 in fluid communication with the distal end 173a of the first nasal prong 173, and a first walled flow path 183 that connects the first inlet port 181 and the first outlet port 182. The first inlet port 181 and the first outlet port 182 of the first breathing gas conduit 180 are contiguous with the first tubing 171 of the nasal cannula 170. First flow path 183 comprises a first luminal interior surface 184 and a first exterior surface 185. The first exterior surface 185 is divided into a first distal exterior surface 185a and a first proximal exterior surface 185b, as shown in FIG. 1A.

Similarly, second breathing gas conduit 190 comprises a second inlet port 191 in fluid communication with the second lumen of the second tubing 172, a second outlet port 192 in fluid communication with the distal end 174a of the second nasal prong 174, and a second walled flow path 193 that connects the first inlet port 191 and the first outlet port 192. The second inlet port 191 and the second outlet port 192 of the second breathing gas conduit 190 are contiguous with the second tubing 172 of the nasal cannula 170. Second flow path 193 comprises a second luminal interior surface 194 and a second exterior surface 195. The second exterior surface 195 is divided into a second distal exterior surface 195a and a second proximal exterior surface 195b, also shown in FIG. 1A.

When the nasal cannula 170 is affixed to a patient, the first nasal prong 173 is positioned in a nare of the patient while the second nasal prong 174 is positioned in the other nare of the patient. In this position, the first proximal exterior surface 185b of the breathing gas conduit 180 is positioned adjacent the patient and between the first distal exterior surface 185a of the breathing gas conduit 180 and the proximal tip 173b of the nasal prong 173. Similarly, when the cannula 170 is attached to the patient, the second proximal exterior surface 195b of the breathing gas conduit 190 is positioned adjacent the patient and between the second distal exterior surface 195a of the breathing gas conduit 190 and the proximal tip 174b of the nasal prong 174. Once the nasal cannula 170 is attached to the patient, the first lumen of the first tubing 171 will be in fluid communication with the first breathing gas conduit 180 and the first nasal prong 173, and the second lumen of the second tubing 172 will be in fluid communication with the second breathing gas conduit 190 and the second nasal prong 174, thereby enabling the heated and humidified breathing gas generated at the capital unit 110 to be provided to the patient.

While the above description of the breathing gas conduits 180 and 190 relates to the nasal cannula 170 in FIG. 1A, the concepts relating to breathing gas conduits in cannulas and nasal prongs may also be applied to all the cannulas described in the present disclosure.

Figure 2:
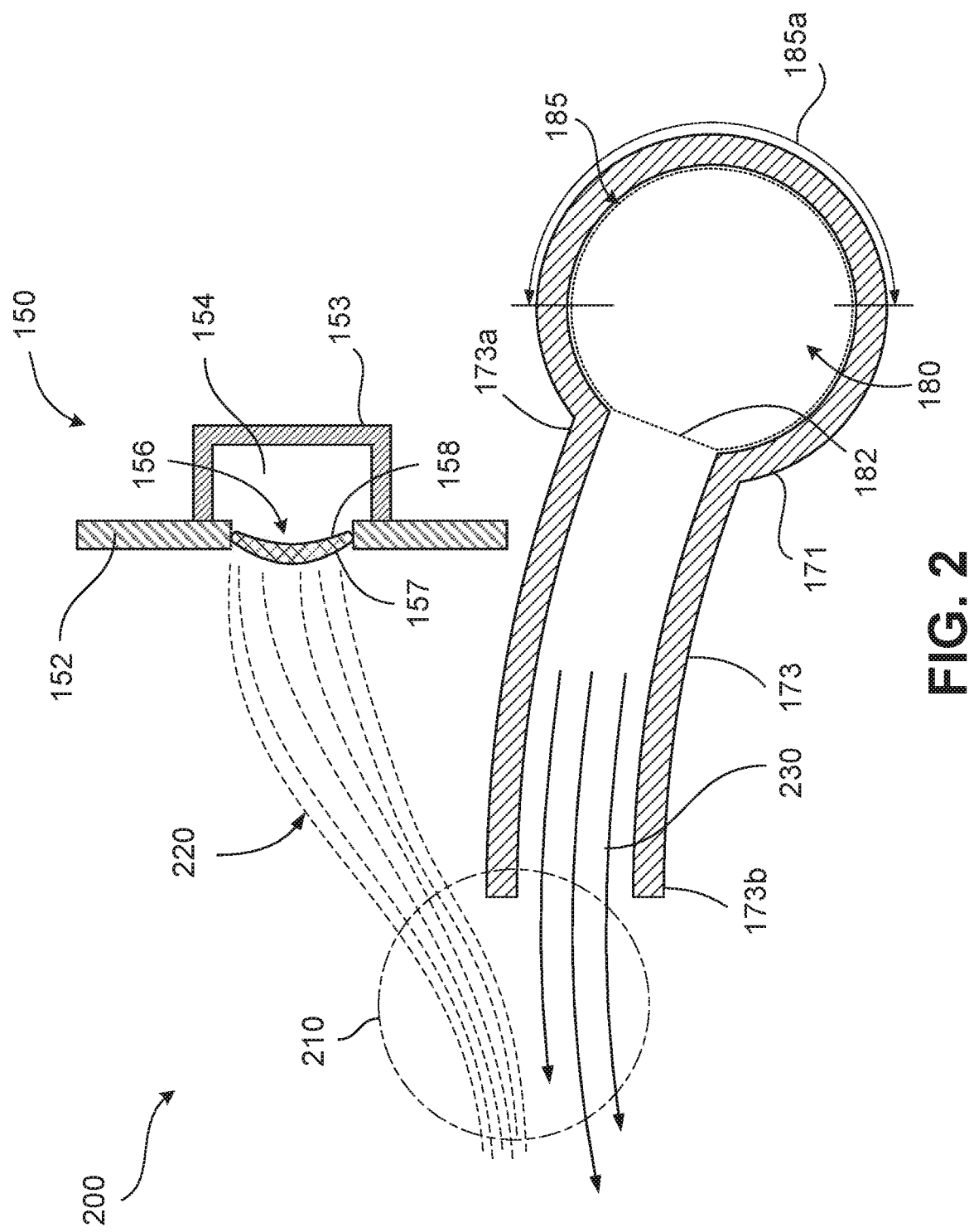
FIG. 2 shows an illustrative cross sectional side view of the cannula based nebulizer of FIG. 1A.

FIG. 2 illustrates a cross section of the nebulizer 150 and cannula 170. It will be understood that while FIG. 2 illustrates the use of nasal cannula 170 having integral prongs 173, 174, any suitable nasal cannula may be used. For example, the nasal cannula 120 and nosepiece 130 illustrated in FIG. 1 may be used instead of nasal cannula 170. In FIG. 2, nebulizer 150 is positioned in close proximity to the breathing gas conduit 180 of the nasal cannula 170 (see FIG. 1A). Nebulizer 150 comprises a mesh 156 and an input transducer 152 attached to the mesh 156. The mesh 156 has a first surface 157 and a second surface 158. The second surface 158 of the mesh 156 is arranged to be in contact with liquid medicament contained in a reservoir 153 at all times. The mesh 156 may have microscopic holes formed therein such that the mesh blocks the passage of liquid when the mesh is in a rest state and allows the passage of liquid when the mesh is in a distorted state. In some embodiments, the mesh 156 may comprise a metal alloy, to give the rigidity, mass, durability and inert chemical properties required for the aerosolization of different drug formulations. In certain embodiments, the mesh 156 may comprise a metal such as platinum, palladium, nickel and stainless steel, for example. In other embodiments, any metal that facilitates the fabrication of consistently sized holes can be used. According to some embodiments, in general, the mesh 156 may have holes with a diameter in the range of approximately 0.10 μm to approximately 50 μm. With such a configuration, resulting medicament droplets have a diameter in the range of approximately 1.0 μm to approximately 5.0 μm. In certain embodiments, the mesh 156 may have thickness in the range of approximately 0.02 mm to approximately 0.4 mm. In other embodiments, the mesh 156 may have any thickness that enables it to vibrate between a rest state and a distorted state. The input transducer 152 may be a piezoelectric element, such as a piezoelectric ceramic, e.g., lead zirconate titanate (PZT), that is capable of transforming electrical energy (such as an electrical voltage) to mechanical energy (such as expansion and contraction forces). In some embodiments the mesh 156 may be circular shaped and the piezoelectric element 152 may be in the form of a piezoelectric ring that encompasses the mesh 156. The mesh 156 may be attached to the piezoelectric ring 152 at all points along the circumference of the mesh 156.

In some embodiments, an alternating voltage is supplied from a power source contained within the signal generator 160 to the piezoelectric ring 152 via connection cable 165. The alternating voltage causes the piezoelectric ring 152 to periodically contract from a rest state to a radially decreased state and back to the rest state. Due to the circumferential attachment of the mesh 156 to the piezoelectric ring 152, the contraction of the piezoelectric ring 152 to the radially decreased state causes the mesh 156 to distort or bow (as shown in FIG. 2). When the piezoelectric ring 152 returns to its rest state, the mesh 156 correspondingly returns to a rest state in which the mesh 156 is not distorted or bowed. The periodic contraction and expansion of the piezoelectric ring 152 therefore causes the mesh 156 to vibrate between a distorted state and a rest state.

When the mesh 156 is in the rest state, liquid medicament from the reservoir 153 is not allowed through the hoes in the mesh 156. When the mesh 156 is in the distorted state, liquid medicament from the reservoir 153 is allowed though the holes in the mesh 156. At the first surface 157 of the vibrating mesh 156, the atomized medicament will grow into drops at each hole in the mesh 156 due to the surface tension of the liquid medicament. The drops will increase in size until the expelling forces arising from the movement of the vibrating mesh 156 and the mass of each drop exceeds a holding force determined by the size of the holes in mesh 156 and the surface tension of the liquid medicament. The drops are then expelled from the first surface 157 of the mesh 156 as an aerosol 220 as depicted in FIG. 2.

In FIG. 2, a flow 230 of heated and humidified gas is provided for inhalation by the patient via nasal prong 173. The flow of heated and humidified gas may be provided by the capital unit 110 in FIG. 1. As previously mentioned, the vibrating mesh 156 of the nebulizer 150 may be located in close proximity to the breathing gas conduit 180 of nasal cannula 170. In certain embodiments, the vibrating mesh 156 may be positioned at a nebulizing distance measured from the proximal end 173b of the nasal prong 173 to the distal exterior surface 185a of the breathing gas conduit 180. The resulting flow of breathing gas 230 from the proximal end 173b of the nasal prong 173 would cause the aerosol 220 generated from the first surface 157 of the vibrating mesh 156 to be drawn into the flow of breathing gas 230 slipstream. The slipstream effect is therefore used to entrain the aerosolized medicament in the flow of breathing gas, in a manner similar to that used in U.S. Pat. No. 9,333,317, the contents of which are hereby incorporated by reference in their entirety. The introduction of aerosol 220 into the flow of breathing gas 230 would occur at an entrainment zone 210 located proximal to the proximal tip 173b of the nasal prong 173, thereby causing the aerosol 220 to be inhaled by the patient along with the heated and humidified gas 230. By locating the screen in close proximity to the nasal prong 173 and orienting it so that the initial velocity of the particles is directed towards the entrainment zone 210 at the proximal tip 173b of the prong 173, the aerosolized medicament can be introduced into the flow of heated and humidified gas without using any conduits at all.

Thus, according to the present disclosure, the aerosolized medicament 220 is generated adjacent to the breathing gas conduit 180 into the atmosphere. The aerosolized medicament 220 is then entrained into the flow of heated and humidified breathing gas 230 by the slipstream effect at an entrainment zone located proximal to the proximal tip 173b of the nasal prong 173. The generation of aerosol in such close proximity to the nasal prong removes the possibility of the aerosolized medicament impacting of the inner walls of the meandering nasal tubing if the aerosol was generated at the capital unit 110 or away from the nasal cannula 170. This minimizes rainout from occurring in the nasal cannula 170. According to certain embodiments of the present disclosure, the arrangement of the vibrating mesh nebulizer 150 with respect to the nasal cannula 170 as described in the foregoing results in less than any of: about 50%, about 45%, about 40%, about 35%, about 30%, about 25%, about 20%, about 15%, about 10%, about 5%, and about 0%, of the aerosol coalescing into droplets and rain-out in the nasal cannula 170.

Figure 2A:
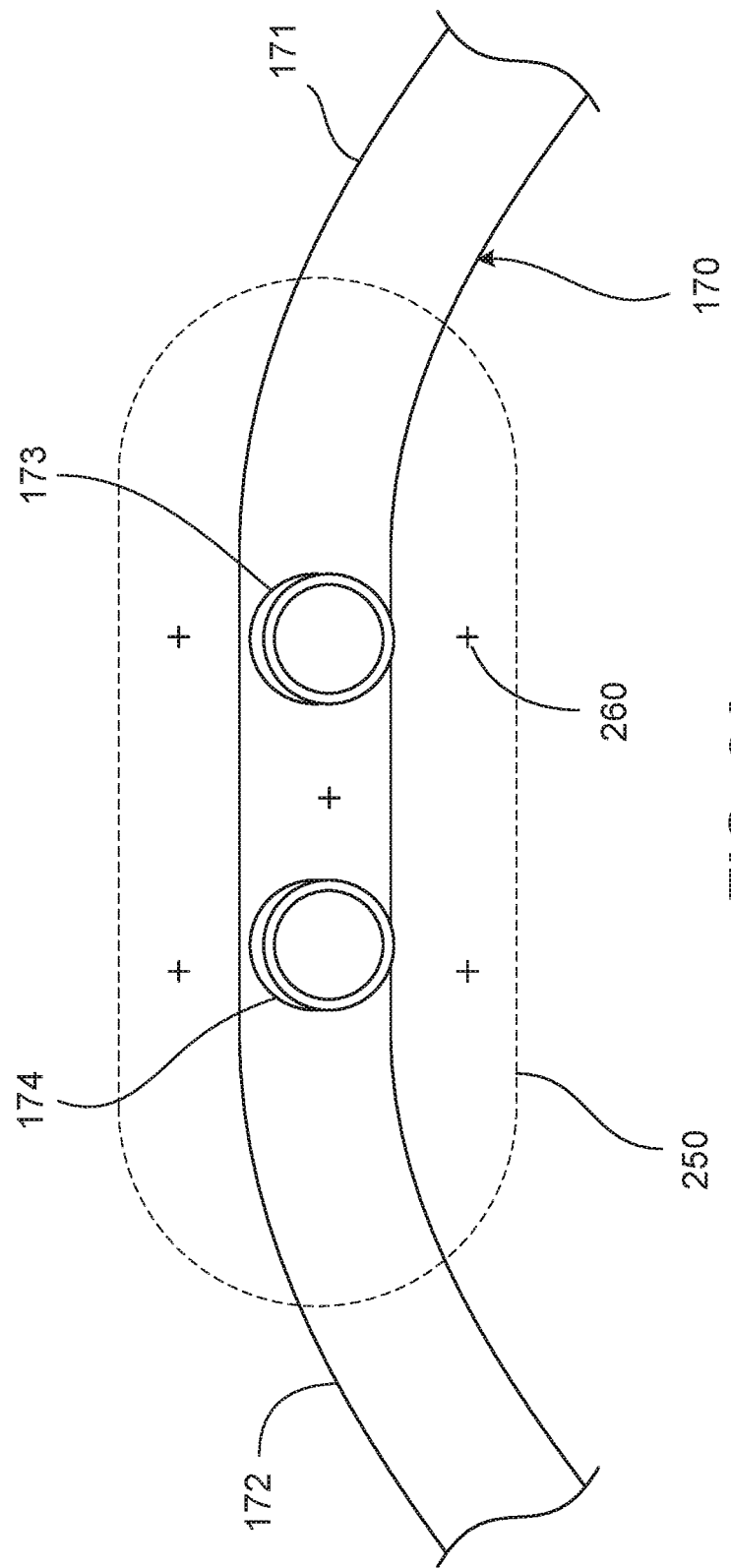
FIG. 2A shows an illustrative front view of the nasal cannula of FIG. 1A.

While it has been described in the foregoing that the vibrating mesh 156 of the nebulizer 150 may be located adjacent to the breathing gas conduit 180 of nasal cannula 170 to achieve entrainment of the aerosol 220 in an entrainment zone 210 located at the proximal tip 173b of the nasal prong 173, the vibrating mesh 156 may be located elsewhere relative to the nasal prongs 173, 174 without deviating from the scope of the present disclosure. FIG. 2A illustrates a front view of the nasal cannula 170 of FIG. 1A. FIG. 2A demarcates a boundary zone 250 of possible locations for the vibrating mesh 156 of the nebulizer such that the generated aerosol stream 220 will be entrained with a flow of heated and humidified gas at the proximal tip 173b, 174b of at least one nasal prong 173, 174. Locations 260 within the boundary region 250 marked with a '+' indicate the position where the vibrating mesh 156 of the nebulizer is to be located.

For example, and with reference to FIG. 1A, the vibrating mesh 156 may be positioned distal of the proximal tip 173b of the nasal prong 174. Alternatively, the vibrating mesh 156 may be positioned between the distal exterior surface 185a of the conduit 180 and the proximal tip 173b of the nasal prong 173. As a further example, the vibrating mesh 156 may be positioned on top of the breathing gas conduit 180. In one example, the vibrating mesh may also be positioned axially between the proximal tip 173b of the nasal prong 173 and the distal end 173a of the nasal prong 173. In another example, the vibrating mesh may be positioned at the distal exterior surface 185a of the breathing gas conduit 180. In a further example, the vibrating mesh may be positioned at the proximal exterior surface 185b of the breathing gas conduit. In another example, the vibrating mesh may be positioned adjacent to the distal exterior surface 185a of the breathing gas conduit 180. The above exemplary positions of the vibrating mesh 156 of the nebulizer 150 relative to the cannula 170 are with reference to nasal prong 173 and breathing gas conduit 180 of cannula 170. However it should be understood that the above exemplified positions could also be taken with respect to nasal prong 174 and breathing gas conduit 190 (see FIG. 1A) of cannula 170, with respect to both nasal prongs 173, 174 of cannula 170 (i.e. between the prongs), or with respect to nosepiece 130 of nasal cannula 120 (see FIG. 1).

Figure 3:
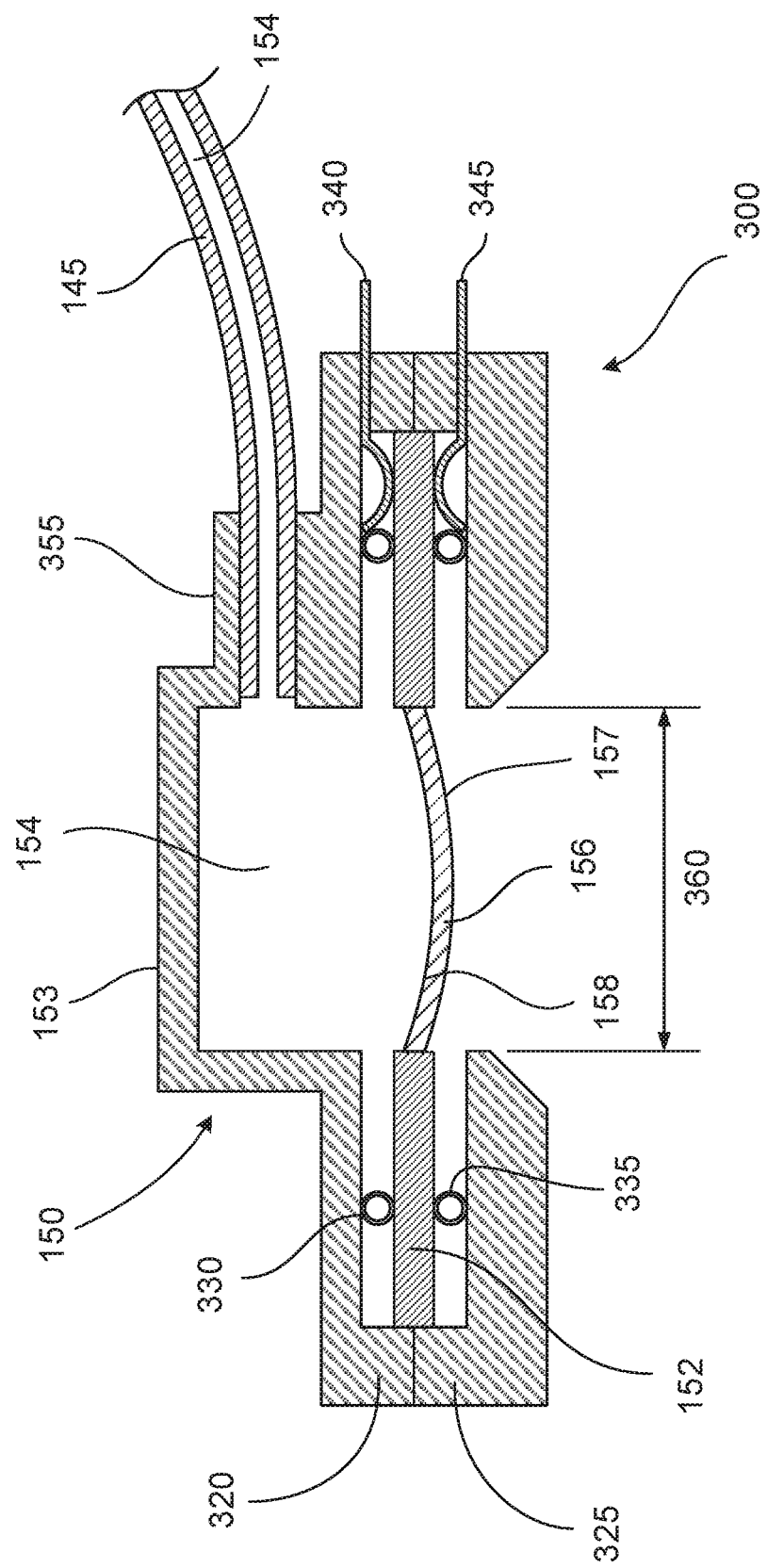
FIG. 3 shows an illustrative cross sectional view of the cannula based nebulizer of FIG. 2.

FIG. 3 illustrates an exemplary embodiment of a nebulizer 300 comprising the vibrating mesh 156 of FIG. 2 for attachment to a cannula. The embodiment in FIG. 3 retains the features of the vibrating mesh nebulizer 150 as described above in relation to FIG. 2. In FIG. 3, the piezoelectric ring 152 is contained in a housing comprising a first section 320 and a second section 325. The first section 320 includes the reservoir 153 for containing the liquid medicament 154 such that the liquid medicament 154 is in contact with the second surface 158 of the mesh 156. The first section 320 also includes a medicament port 355 for attaching a feed line 145 from the supply bag 140 (as shown in FIG. 1). The feed line 145 allows the liquid medicament 154 to be flowed into the reservoir 153 for generating the aerosol stream 220. The second section 320 includes an opening 360 that aligns with the first surface 157 of mesh 156 such that any aerosol generated by the mesh 156 is emitted via opening 360. To ensure high efficiency of aerosol generation, opening 360 is configured such that the diameter of the opening 360 is at least the same as or larger than the diameter of the mesh 156. This ensures that no aerosol is trapped on an inner facing surface of the second section 320. In some embodiments, the liquid medicament 154 may be flowed from the supply bag 140 into the reservoir 153 under the effect of gravity. Alternatively, the liquid medicament 154 may be pumped into the reservoir 153 with a pressure-based pump, such as, for example, a centrifugal pump. In certain embodiments, the liquid medicament may be contained in a pressurized portable vial located on the patient (behind the patient's ear, for example), with a feed line 145 to the nebulizer 300, thereby increasing the portability of the nebulizer 300.

The first and second sections 320, 325 of the nebulizer housing may include O-rings 330, 335 to maintain a liquid tight seal between the liquid medicament 154 in the reservoir 153 and the rest of the nebulizer 300. Further, the first and second sections 320, 325 of the nebulizer housing may include electrical contacts 340, 345 that separately extend from a first surface and a second surface of the piezoelectric ring 152 to the exterior of the nebulizer housing 320, 325. Such an arrangement allows electrical signals from the signal generator 160 to be easily fed to the nebulizer 300 using cable 165 (see FIG. 1).

In some embodiments, housing 320, 325 of nebulizer 300 may be fabricated in a material comprising polyvinyl chloride (PVC) plastic, plastisol, vinyl, silicone, non-latex rubber, an elastomer, ethylene vinyl acetate (EVA), styrene-butadiene copolymer (SBC), polyether ether ketone (PEEK), a polyether block amide (such as PEBAX), a polyethylene material, a high-density polyethylene (HDPE) material, a medium-density polyethylene (MDPE) material, a low-density polyethylene (LDPE) material, a crack-resistant material, a material with a low coefficient of friction, a material less than 70 Durometer Shore A, or any other suitable material).

The nebulizer in FIG. 3 is contained in a housing 320, 325, has an input feed line 145 for liquid medicament, and allows for electrical connection with cable 165 of signal generator 160 (see FIG. 1). These features result in nebulizer 300 being portable and easily attached to a nasal cannula, such as cannulas 120 in FIG. 1 and cannula 170 in FIG. 1A, thereby enabling the vibrating mesh 156 contained in the housing 320, 325 to be orientated relative to a nasal cannula as described in the foregoing.

Figure 4:
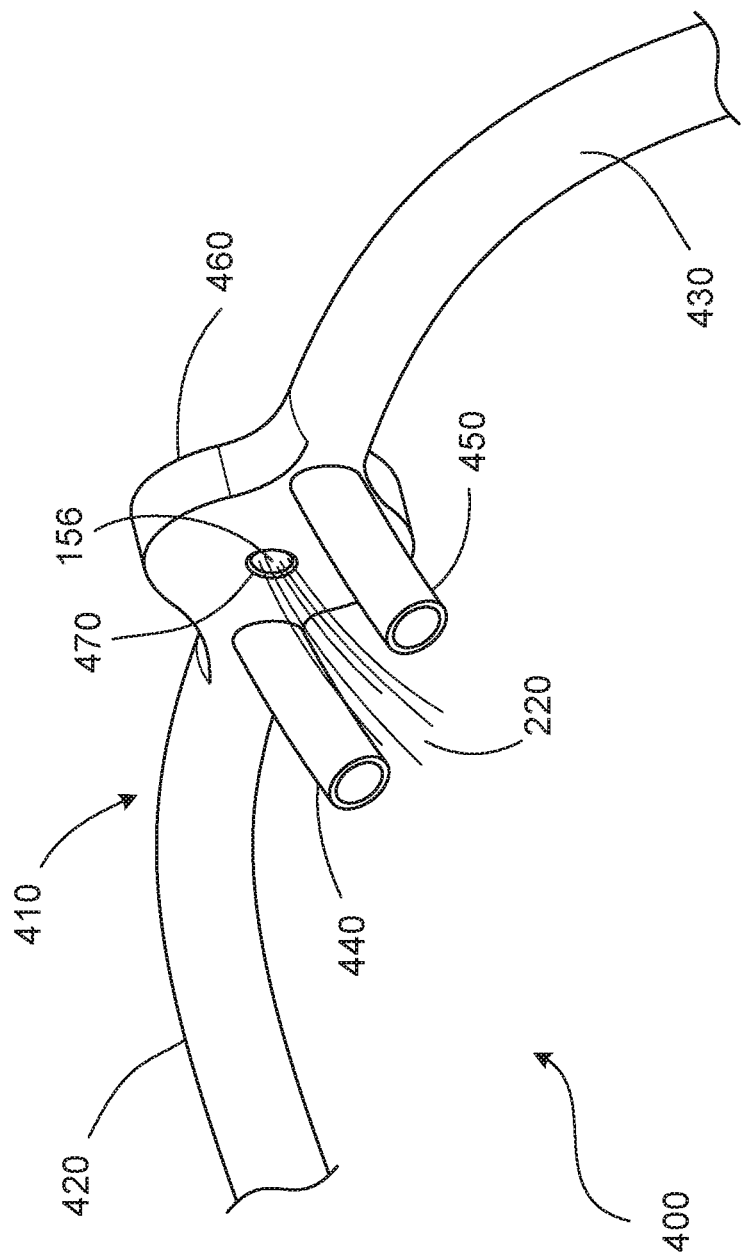
FIG. 4 shows an illustrative perspective view of a first embodiment of the cannula based nebulizer of FIG. 1.

FIG. 4 illustrates an exemplary embodiment 400 of the present disclosure in which the nebulizer 300 in FIG. 3 is coupled to a nasal cannula 410. As with cannula 120 in FIG. 1 and cannula 170 in FIG. 1A, cannula 410 may comprise a first tubing 420, a second tubing 430, a first nasal prong 440, and a second nasal prong 450. Although not shown in FIG. 4, a flow of heated and humidified gas may be provided to the cannula 410 via a delivery tube similar to delivery tube 150 shown in FIG. 1. The first tubing 420 has a first lumen and the second tubing 430 has a second lumen, both lumens allowing the flow of heated and humidified gas therethrough. The first nasal prong 440 and the second nasal prong 450 are integrally formed in cannula 410 such that a distal end of the first nasal prong 440 is attached to the first tubing 420, and a distal end of the second nasal prong 450 is attached to the second tubing 430. The first nasal prong 440 may be positioned in one of the patient's nares and is in fluid communication with the first lumen of the first tubing 420 such that flow of heated and humidified gas flowing through the first lumen is delivered to the patient at a proximal tip of the first nasal prong 440. Similarly, the second nasal prong 450 may be positioned in the patient's other nare and is in fluid communication with the second lumen of the second tubing 430 such that flow of heated and humidified gas flowing through the second lumen is delivered to the patient at a proximal tip of the second nasal prong 450.

Cannula 410 may comprise a housing 460 integrally formed in a bridge portion of the cannula between the first nasal prong 440 and the second nasal prong 450. Such integral formation may be achieved by molding the housing 460 with the body of cannula 410 during fabrication. Housing 460 may be a shell that enables the nebulizer 300 to attach to cannula 410. In such a configuration, the first and second lumens are not in fluid communication with each other in the bridge portion of the cannula between the nasal prongs 440, 450. Attachment of the nebulizer 300 to housing 460 may be provided by any arrangement that releasably attaches the nebulizer 300 to the housing 460. For example the attachment between housing 460 and the nebulizer 300 may be a snap fit. Housing 460 may additionally comprise a port 470 positioned at any point between the first nasal prong 440 and the second nasal prong 450. Port 470 defines an opening in the housing 460. Port 470 is positioned such that the opening in the housing 460 is aligned with the first surface 157 of the vibrating mesh 156 of nebulizer 300 so as to expose the first surface 157 to the atmosphere. The diameter of the port 470 may be greater than the diameter of the mesh 156 so as to ensure that all the aerosol 220 generated at the first surface 157 of the vibrating mesh 156 is emitted from the cannula 410 and not caught between the housing 460 and the nebulizer 300. In some embodiments, the housing 460 is positioned between the first nasal prong 440 and the second nasal prong 450. In some embodiments, the nasal prongs 440, 450 may be formed in a nosepiece (similar to nosepiece 130 in FIG. 1) that is in fluid communication with the first and second tubings 420, 430. In such a configuration, the housing 460 may be formed in the nosepiece. In some embodiments, the nasal prongs may be of the same length. In other embodiments, one nasal prong may be longer than the other.

When the nebulizer 300 is coupled to the housing 460, the position of the mesh 156 will be fixed relative to the cannula 410 and the first and second nasal prongs 440, 450. The present disclosure includes variations in the design of the housing 460 and location of the housing 460 on the cannula 410 such that the position of the mesh 156 relative the features of the cannula 410 may be varied as described in the foregoing with respect to FIGS. 1A and 2 so as to achieve entrainment of the aerosol, generated at the mesh 156, with the flow of heated and humidified gas at the proximal tip of at least one nasal prong.

As described in the foregoing with respect to FIG. 2, in the exemplary embodiment of FIG. 4, the aerosol stream 220 is entrained into the flow of heated and humidified gas by the slipstream effect at an entrainment zone located proximal to the proximal tip of any or both of the nasal prongs 440, 450. Such entrainment of generated aerosolized medicament removes the possibility of the aerosolized medicament impacting on surfaces in meandering nasal tubing if the aerosol was generated at the capital unit 110 or away from the nasal cannula 410. This minimizes rainout from occurring in the nasal cannula 410. According to certain embodiments of the present disclosure, the arrangement of the nebulizer 300 with respect to the nasal cannula 410 may result in less than 5% of the aerosol coalescing into droplets in the nasal cannula 410.

The integrated housing 460 in cannula 410 enables the nebulizer 300 to easily (and releasably) attach to the cannula 410. This makes for a light and less cumbersome nebulizer cannula that can be easily attached to the patient. As the nebulizer 300 is effectively locked in position within the cannula housing 460, operation of the nebulizer 300 and the direction of flow of the aerosol 220 is less likely to be affected by movement of the patient.

Figure 5:
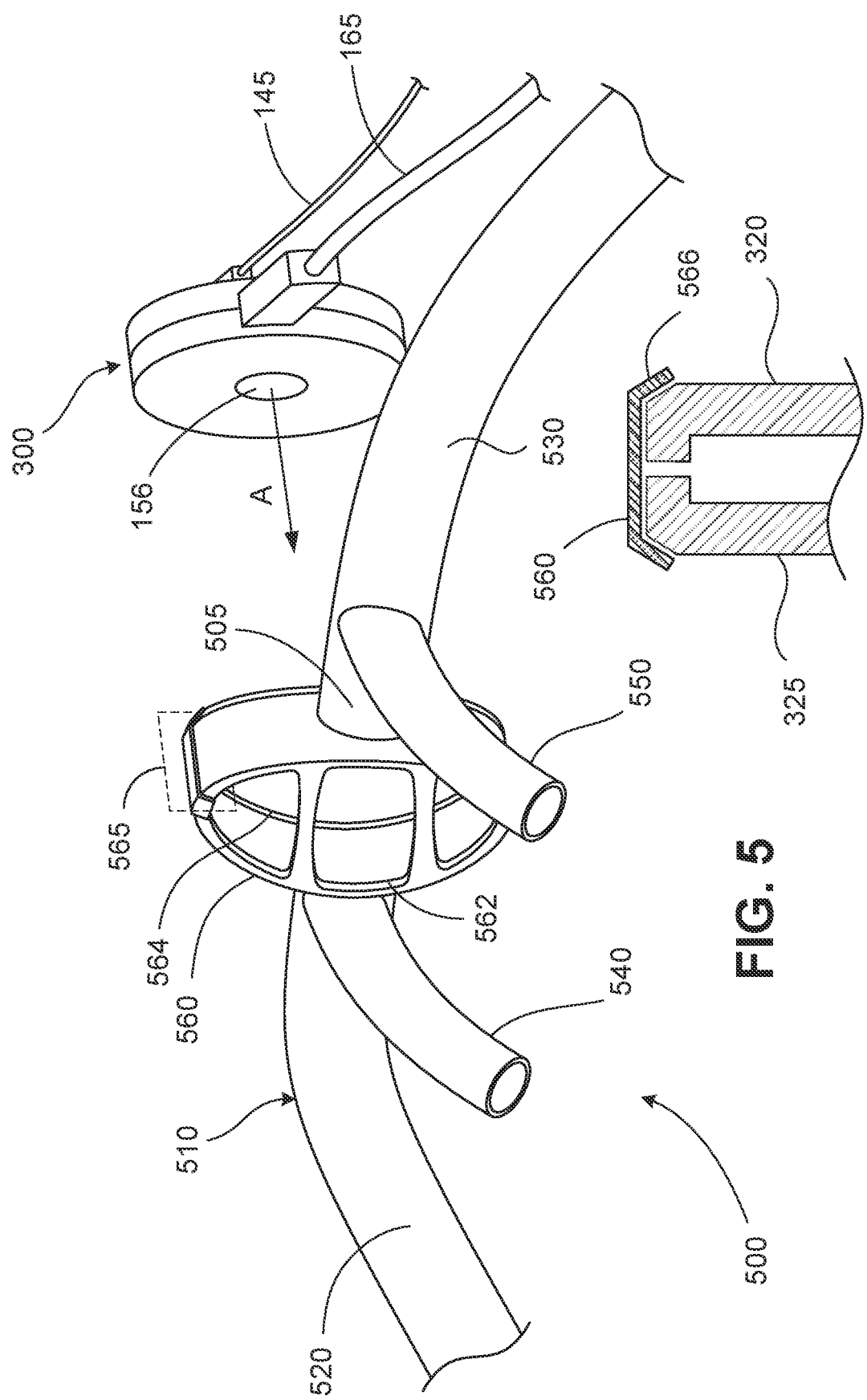
FIG. 5 shows an illustrative perspective integrated snap-fit cannula based nebulizer according to an embodiment of the present disclosure.

FIG. 5 illustrates a further exemplary embodiment 500 of the present disclosure in which the nebulizer 300 is coupled to a nasal cannula 510. As with cannulas 120, 170 and 410 discussed in the foregoing, cannula 510 may comprise a first tubing 520, a second tubing 530, a first nasal prong 540, and a second nasal prong 550. Although not shown in FIG. 5, a flow of heated and humidified gas may be provided to the cannula 510 via a delivery tube similar to delivery tube 150 shown in FIG. 1. The first tubing 510 has a first lumen and the second tubing 520 has a second lumen, both lumens allowing the flow of heated and humidified gas therethrough. The first nasal prong 540 and the second nasal prong 550 are integrally formed in cannula 510 such that a distal end of the first nasal prong 540 is attached to the first tubing 520, and a distal end of the second nasal prong 550 is attached to the second tubing 530. The first nasal prong 540 may be positioned in one of the patient's nares and is in fluid communication with the first lumen of the first tubing 520 such that flow of heated and humidified gas flowing through the first lumen is delivered to the patient at the proximal tip of the first nasal prong 540. Similarly, the second nasal prong 550 may be positioned in the patient's other nare and is in fluid communication with the second lumen of the second tubing 530 such that flow of heated and humidified gas flowing through the second lumen is delivered to the patient at the proximal tip of the second nasal prong 550. In some embodiments, the nasal prongs 540, 550 may be formed in a nosepiece (similar to nosepiece 130 in FIG. 1) that is in fluid communication with the first and second tubings 520, 530. In some embodiments, nasal cannula 510 may further comprise a bridge 505 which separates the first lumen from the second lumen. In further embodiments, the bridge 505 may have a lumen therethrough connecting the first lumen to the second lumen such that all lumens are in fluid communication with each other and the nasal prongs 540, 550.

Cannula 510 may comprise a housing 560 that is attached to the bridge of the cannula between the first nasal prong 540 and the second nasal prong 550. Such attachment may be provided by any arrangement that releasably attaches the housing 560 to the nasal cannula 510. For example the housing 560 may have hooks formed therein that clip onto the bridge 505 of the nasal cannula 510. In some embodiments, housing 560 may be separated in multiple sections that snap together around the bridge 505 of the cannula 510 thereby securing the housing 560 to the nasal cannula 510. Housing 560 forms a shell or cage that enables the nebulizer 300 in FIG. 3 to be secured in a position relative to cannula 510. As with the integral housing 460 in FIG. 4, the attachment of the nebulizer 300 to the housing 560 may be provided by a friction or interference fit, for example. In certain embodiments where the housing 560 is formed in multiple sections that snap together, the nebulizer 300 may simply be encased in the space formed by the multiple sections of the housing 560 whereby the multiple sections hold the nebulizer 300 in a fixed position relative to the cannula 510. Housing 560 may have at least one opening 562 on its proximal surface for the propulsion of aerosol generated by the nebulizer 300. Housing 560 may also have at least one opening 564 on its distal surface for inserting the nebulizer 300. In some embodiments, a short conduit (not shown) may be attached to the opening on the proximal surface of the housing 560 to direct the aerosol generated by the nebulizer 300 to the proximal tip of any one of the nasal prongs 540, 550 such that a greater proportion of aerosol is entrained in the flow of heat and humidified gas.

FIG. 5A illustrates a cross-section of the housing 560 taken about plane 565 in FIG. 5 when the nebulizer 300 is attached to the housing 560. Housing 560 may have a lip 566 on one or both of its proximal and distal facing edges. Housing 560 may be very closely shaped and dimensioned to the nebulizer 300 to ensure an interference fit between the housing 560 and the nebulizer 300 such that lip 566 elastically deforms to allow the nebulizer 300 to be pushed or popped into the housing 560, as indicated by arrow A in FIG. 5. When the nebulizer 300 is in position within housing 560, lip 566 grips onto the first and second sections 320, 325 of the housing of nebulizer 300. The elastic deformation of the lip 566 allows the nebulizer 300 to be securely positioned in the housing 560.

When the nebulizer 300 is coupled to the housing 560, the position of the mesh 156 will be fixed relative to the cannula 510 and the first and second nasal prongs 540, 550. The present disclosure includes variations in the design of the housing 560 and point of attachment of the housing 560 to the cannula 510 such that the position of the mesh 156 relative the features of the cannula 510 may be varied as described in the foregoing with respect to FIGS. 1A and 2 so as to achieve entrainment of the aerosol, generated at the mesh 156, with the flow of heated and humidified gas at the proximal tip of at least one nasal prong.

As described in the foregoing with respect to FIG. 2, in the exemplary embodiment of FIG. 5, the aerosol stream generated by the nebulizer 300 is entrained into the flow of heated and humidified gas by the slipstream effect at an entrainment zone located proximal to the proximal tip of any or both of the nasal prongs 540, 550. Such entrainment of generated aerosolized medicament removes the possibility of the aerosolized medicament impacting on surfaces in meandering nasal tubing if the aerosol was generated at the capital unit 110 or away from the nasal cannula 510. This minimizes rainout from occurring in the nasal cannula 510. According to certain embodiments of the present disclosure, the arrangement of the nebulizer 300 with respect to the nasal cannula 510 may result in less than any of: about 50%, about 45%, about 40%, about 35%, about 30%, about 25%, about 20%, about 15%, about 10%, and about 5%, of the aerosol coalescing into droplets in the nasal cannula 510.

Housing 560 is a separate entity from nasal cannula 510. This enables the housing 560 to be attached to any nasal cannula, in an adaptor-like manner for the positioning of the vibrating mesh nebulizer 300 so as to generate aerosol proximate to the nasal prongs and to entrain the generated aerosol into the flow of gas at the proximal tip of at least one nasal prong, as described in the foregoing disclosure. In this manner, no specialized cannula design is necessary thus making the embodiment of FIG. 5 adaptable to nasal cannulas available in the art. Additionally, as the nebulizer 300 is locked in position within the cannula housing 560, operation of the nebulizer 300 and the direction of flow of the aerosol is less likely to be affected by movement of the patient.

Figure 6:
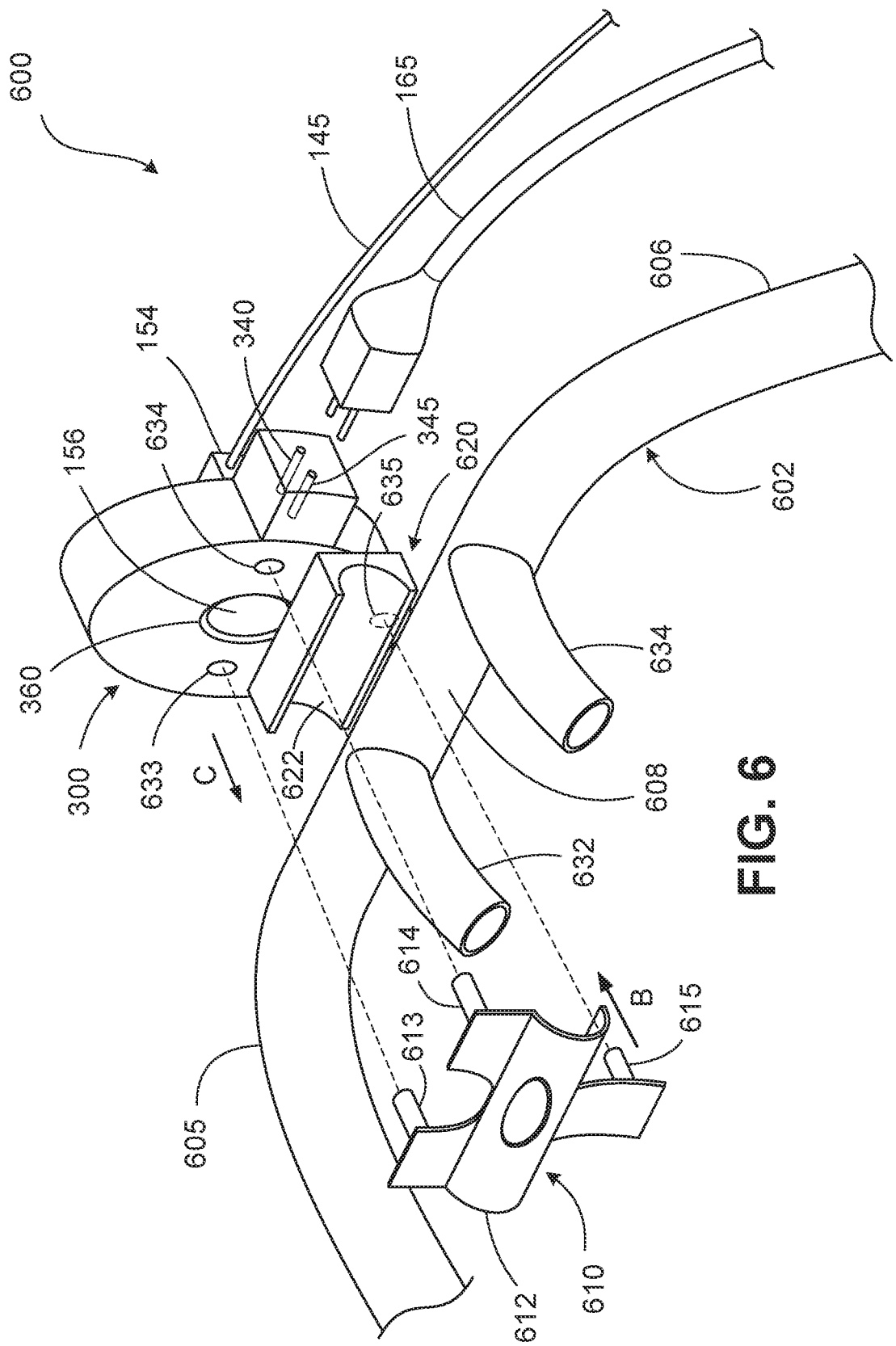
FIG. 6 shows an illustrative expanded view of an integrated cannula based nebulizer according to an embodiment of the present disclosure.

FIG. 6 illustrates a further exemplary embodiment 600 of the present disclosure in which the nebulizer 300 is coupled to a nasal cannula 602. As with cannulas 120, 170, 410 and 510 discussed in the foregoing, cannula 602 may comprise a first tubing 605, a second tubing 606, a first nasal prong 632, and a second nasal prong 634. Although not shown in FIG. 6, a flow of heated and humidified gas may be provided to the cannula 602 via a delivery tube similar to delivery tube 150 shown in FIG. 1. The first tubing 605 has a first lumen and the second tubing 606 has a second lumen, both lumens allowing the flow of heated and humidified gas therethrough. The first nasal prong 632 and the second nasal prong 634 are integrally formed in cannula 602 such that the distal end of the first nasal prong 632 is attached to the first tubing 605, and the distal end of the second nasal prong 634 is attached to the second tubing 606. The first nasal prong 632 may be positioned in one of the patient's nares and is in fluid communication with the first lumen of the first tubing 605 such that flow of heated and humidified gas flowing through the first lumen is delivered to the patient at the proximal tip of the first nasal prong 632. Similarly, the second nasal prong 634 may be positioned in the patient's other nare and is in fluid communication with the second lumen of the second tubing 606 such that flow of heated and humidified gas flowing through the second lumen is delivered to the patient at the proximal tip of the second nasal prong 634. In some embodiments, the nasal prongs 632, 634 may be formed in a nosepiece (similar to nosepiece 130 in FIG. 1) that is in fluid communication with the first and second tubings 605, 606. In certain embodiments, nasal cannula 602 may further comprise a bridge 608 which separates the first lumen from the second lumen. In further embodiments, the bridge 608 may have a lumen therethrough connecting the first lumen to the second lumen such that all lumens are in fluid communication with each other and the nasal prongs 632, 634.

Cannula 602 may further comprise a first coupling part 610 and a second coupling part 620. First coupling part 610 may be provided with a first flexible cuff 612 and attachment pins 613-615, and second coupling part 620 may be provided with a second cuff 622. The distal outer surface of the second cuff 622 may have a flat surface that may be attached to the proximal outer surface of a nebulizer, such as the vibrating mesh nebulizer 300 of FIG. 3. Such attachment may be by way of epoxy resin or glue, for example. As described in the foregoing, nebulizer 300 comprises a vibrating mesh 156 that is capable of generating an aerosolized medicament via opening 360. Housing sections 320, 325 of nebulizer 300 are provided with recesses 633-635 that align with pins 613-615 of the first coupling part 620. In order to attach the nebulizer 300 to cannula 602 the first coupling part 610 is positioned on the cannula 602 as indicated by arrow B and the second coupling part 620 (attached to the nebulizer 300) is positioned on the cannula 602 as indicated by arrow C. When in position, the first cuff 612 is contact with a proximal exterior surface of the bridge 608 and the second cuff 622 is in contact with a distal exterior surface of the bridge 608. The pins 613-615 on the first coupling part 610 engage the corresponding recesses 633-635 on the second coupling part 620. Such engagement may be provided by any coupling means, such as a friction or an interference fit, for example. While pins 613-615 and recesses 633-635 are used to attach the nebulizer 300 to the nasal cannula 602, in certain embodiments, the nebulizer 300 may be attached to the nasal cannula 602 by clamps, snap-fit connectors or I-connectors. In some embodiments, the surfaces of the first and second cuffs 612, 622 may be coated with an anti-slip material such that when the first and second coupling parts 610, 620 are attached to the cannula 602 no movement of the nebulizer 300 occurs.

When the nebulizer 300 is held in a fixed position with respect to the cannula 602 by the first and second coupling parts 610, 620, the position of the mesh 156 will be fixed relative to the cannula 602 and the first and second nasal prongs 632, 634. With this arrangement, the aerosol generated by the vibrating mesh 156 will be directed to an entrainment zone at the proximal tip of at least one nasal prong 632, 634 similar to the entrainment zone 210 illustrated in FIG. 2. The present disclosure includes variations in the design of the first and second coupling parts 610, 620, as well as the point of coupling of the first and second coupling parts 610, 620 to the cannula 602, such that the position of the mesh 156 relative the features of the cannula 602 may be varied as described in the foregoing with respect to FIGS. 1A and 2 so as to achieve entrainment of the aerosol, generated at the mesh 156, with the flow of heated and humidified gas at the proximal tip of at least one nasal prong.

As described in the foregoing with respect to FIG. 2, in the exemplary embodiment of FIG. 6, the aerosol stream generated by the nebulizer 300 is entrained into the flow of heated and humidified gas by the slipstream effect at an entrainment zone located proximal to the proximal tip of any or both of the nasal prongs 632, 634. Such entrainment of generated aerosolized medicament removes the possibility of the aerosolized medicament impacting on surfaces in meandering nasal tubing if the aerosol was generated at the capital unit 110 or away from the nasal cannula 602. This minimizes rainout from occurring in the nasal cannula 602. According to certain embodiments of the present disclosure, the arrangement of the nebulizer 300 with respect to the nasal cannula 602 may result in less than any of: about 50%, about 45%, about 40%, about 35%, about 30%, about 25%, about 20%, about 15%, about 10%, and about 5%, of the aerosol coalescing into droplets in the nasal cannula 602.

As with housing 560 in FIG. 5, first and second coupling parts 610, 620 are a separate entity from nasal cannula 602. Additionally, in the embodiment of FIG. 6, the nebulizer 300 can be secured to the second coupling part 620 in advance and before attachment to the nasal cannula 602. The first coupling part 610 is a thin flexible flap that can be attached to the proximal exterior surface of the bridge 608 while the cannula 602 is being used by the patient. Second coupling part 620 can be simply clipped into place when the nebulizer 300 is required. This would cause less disturbance to the patient and would not interrupt the flow of breathing gas to the patient. Further, first and second coupling parts 610, 620 can be attached to any nasal cannula, in an adaptor-like manner for the precise positioning of the vibrating mesh nebulizer 300 so as to entrain the generated aerosol into the flow of gas at the proximal tip of at least one nasal prong, as described in the foregoing disclosure. In this manner, no specialized cannula design is necessary thus making the embodiment of FIG. 6 adaptable to nasal cannulas available in the art. The nebulizer 300 is also securely held in position within first and second coupling parts 610, 620, and so operation of the nebulizer 300 and the direction of flow of the aerosol is less likely to be affected by movement of the patient.

FIG. 7 shows a flowchart of an illustrative method for providing respiratory therapy to a patient. The method 700 begins at step 710 where a source of breathing gas is attached to a nasal cannula. The nasal cannula may have a first tubing, a second tubing, and at least one nasal prong, such as nasal cannulas 120, 170, 410, 510 and 602 as described in the foregoing. In some embodiments, the first and second tubings are connected to a nosepiece having at least one nasal prong. The nasal cannula is attached to the patient such that the nasal prong is positioned in the patient's nares. The source of breathing gas may be attached to the nasal cannula such that a flow of breathing gas is provided to the patient through each of the first and second tubings of the nasal cannula and the nasal prong. The source of breathing gas may be located away from the patient, such as at the capital unit 110, and may be warmed and humidified before being provided to the patient.

At step 720, a nebulizer is attached to the nasal cannula. The nebulizer may comprise a mesh having holes such that when the mesh is in a first state, liquid medicament is not permitted through the holes in the mesh, and when the mesh is in a second state, liquid medicament is permitted to pass though the holes in the mesh. The nebulizer may comprise a piezoelectric ring that surrounds the mesh. The piezoelectric ring may be reactive to an input electric signal so as to cause a change of state of the mesh from the first state to the second state (or vice versa). When the electric signal is alternating in nature, such as an alternating voltage signal, for example, the mesh vibrates thereby generating a stream of aerosolized medicament. The nebulizer may be configured in manner similar to nebulizer 300 as described in the foregoing.

At step 730, the vibrating mesh is positioned relative to the nasal prong by attaching the nebulizer to the nasal cannula. The nebulizer can be attached at any point of the nasal cannula that enables the aerosol stream from the nebulizer to be entrained in the flow of breathing gas at an entrainment zone located at the proximal tip of the nasal prong. Preferred positions of the vibrating mesh relative to the nasal prongs of the nasal cannula have been discussed in the foregoing and in relation to FIGS. 2 and 2A. In these positions, the aerosol is entrained in the flow of breathing gas by the slipstream effect such that the flow of breathing gas emerging from the proximal tip of the nasal prong draws the aerosol particles generated in close proximity to it. Such entrainment of aerosolized medicament in the flow of breathing gas minimizes the possibility of the aerosolized medicament impacting on surfaces in meandering tubing if the aerosol was generated at a capital unit away from the nasal cannula. This minimizes rainout from occurring in the nasal cannula or elsewhere in the system. According to certain embodiments of the present disclosure, the arrangement of the vibrating mesh nebulizer with respect to the nasal cannula may result in less than any of: about 50%, about 45%, about 40%, about 35%, about 30%, about 25%, about 20%, about 15%, about 10%, and about 5%, of the aerosol coalescing into droplets in the nasal cannula. Exemplary configurations of the nasal cannula relative to the nebulizer have been described in relation to FIGS. 4-6 in the foregoing.

Figure 8:
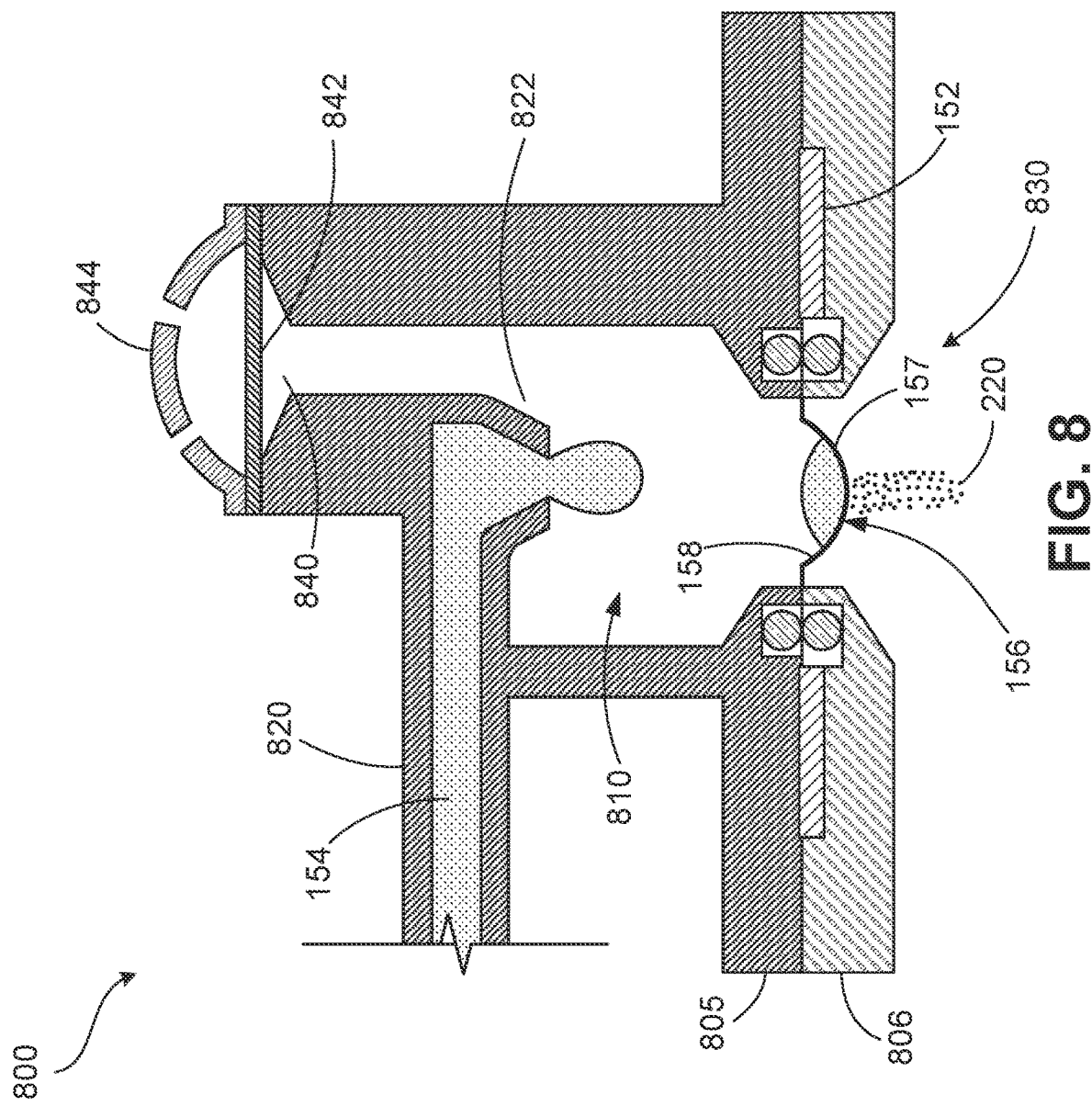
FIG. 8 shows an illustrative cross sectional view of a nebulizer having a remote aerosol reservoir according to an embodiment of the present disclosure.

FIG. 8 illustrates a further exemplary embodiment of a nebulizer 800 comprising a vibrating mesh, such as the vibrating mesh 156 of FIG. 2, for attachment to a cannula, such as any of cannulas 400, 500 and 600 as described in the foregoing. The embodiment in FIG. 8 retains the features of the vibrating mesh nebulizer 150 as described above in relation to FIG. 2 where an electric signal is provided to the piezoelectric element 152 attached to the mesh 156 to cause vibration thereof to generate an aerosol at the first surface 157 of the mesh 156. Nebulizer 800 comprises a housing having a first section 805 and a second section 806. In certain implementations the second section 806 may form part of a nasal cannula or a ventilation mask attached to a patient. In some implementations the first section 805 is configured to couple with the second section 806 using coupling means (such as a magnetic snap fit, for example). The first section 805 includes a chamber 810 that is in fluid communication with an inlet 820, an outlet 830 and a pressure port 840. Inlet 820 defines a drug conduit. A feed tube (such as tube 145 in FIG. 1) is connected to the inlet 820 for the delivery of liquid medicament 154 from a remote reservoir (such as supply bag 140 in FIG. 1) to the chamber 810 via the drug conduit. The liquid medicament is delivered to the chamber 810 using a pump (with limited pressure) or gravity feed. A proximal end of the inlet 820 comprises a nozzle 822. As depicted in FIG. 8, the nozzle 822 has an inner diameter that is smaller than the inlet 820.

The vibrating mesh 156 is positioned at the outlet 830 of the chamber 810 such that the mesh 156 is in vertical alignment with the nozzle 822 so that the termination of the drug conduit is poisoned directly above the mesh 156. In certain implementations, the outlet 830 may be circular. As described in relation to FIG. 2, mesh 156 is mounted on a piezoelectric element 152. In some implementations, the piezoelectric element 152 may be mounted between the first section 805 and the second section 806 of the housing. In certain embodiments, the mating surface of the second section 806 may comprise a groove in which the piezoelectric element 152 sits such that when the first section 805 of the housing is coupled to the second section 806 of the housing, the piezoelectric element is concealed therein. With this arrangement the first surface 157 of the mesh 156 faces outwards for the delivery of aerosolized medicament, and the second surface 158 of the mesh 156 faces the chamber 810.

The pressure port 840 is vertically oriented with respect to the chamber 810 and comprises an opening that vents the chamber 810 to the atmosphere. In some implementations, the pressure port 840 comprises a gas-permeable membrane 842 that is attached to the opening. In certain implementations, the gas-permeable membrane 842 may comprise a Gore-Tex or other Teflon membrane, for example. In other implementations, the pressure port may additionally have vent cover 844 that may be perforated. The gas-permeable membrane 842 and/or the cover 844 facilitate venting the chamber 810 in contact with the second surface 158 of the mesh 156 to the atmosphere.

In FIG. 8, liquid medicament is delivered to the chamber 810 via a pump connected to the feed tube attached to the inlet 820. Here the pump is controlled to operate at a flow rate that is less than the rate at which the vibrating mesh 156 converts the liquid medicament to aerosol. This ensures that the release of liquid medicament from the nozzle 822 is such that only one drop of medicament at a time is present on the mesh 156. Alternatively, if a pump is not used, the liquid medicament drops from the nozzle 822 onto the second surface 153 of the mesh 156 under the action of gravity. In either case, the delivery of liquid medicament to the second surface 153 of the mesh 156 is controlled thereby preventing the drug from being forced through the mesh. Further, while the liquid medicament is delivered to the second surface 153 of the mesh 156, the chamber 810 is vented via the pressure port 840 such that the pressure of the liquid medicament against the mesh 156 is only that of the small head height of the liquid medicament in the reservoir. This prevents the liquid medicament from being pushed through the mesh 156 too quickly (or too slowly), thereby allowing the vibrating mesh to function properly. Thus the nebulizer 800 provides a way to move the liquid medicament to the mesh 156 without generating excess pressure on the mesh 156.

Figure 9:
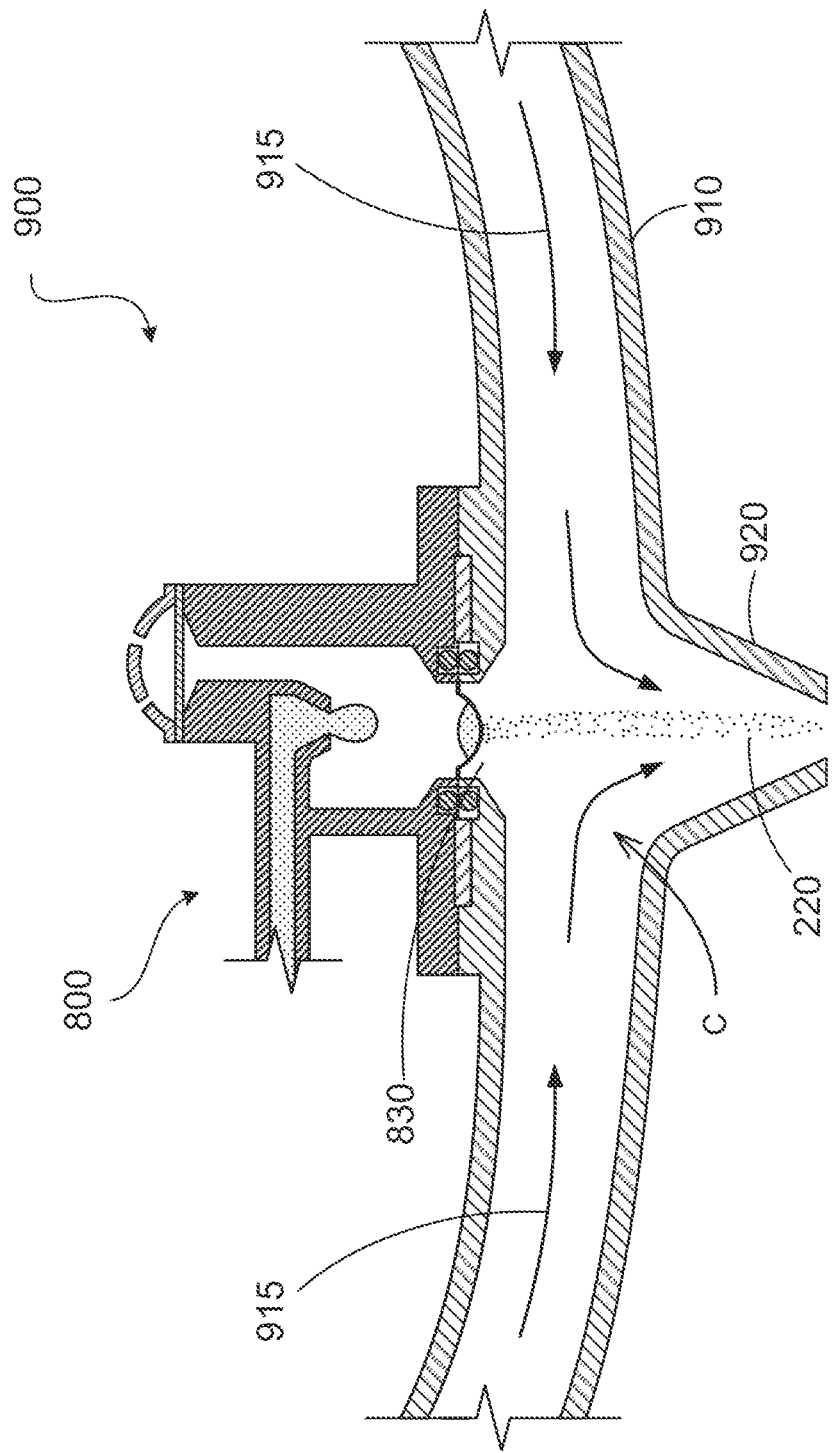
FIG. 9 shows an illustrative cross sectional view of the nebulizer having a remote aerosol reservoir of FIG. 8 mounted onto a cannula.

FIG. 9 illustrates an embodiment 900 of the present disclosure showing the integration of the nebulizer 800 into a patient interface, such as a nasal cannula 910. As an alternate to nasal cannula 910, any of cannulas 400, 500 and 600 as described in the foregoing may be integrated with nebulizer 800. Further, while FIG. 9 shows the nebulizer 800 integrated with a nasal cannula, it will be understood that the nebulizer 800 according to embodiments of the present disclosure may be integrated with any other respiratory patient interface, such as a mask, for example. As shown in FIG. 9, the body of the nasal cannula 910 forms the second portion of the nebulizer 800 and the outlet of the 830 comprises an opening formed in the cannula body. With this arrangement, the mesh 156 of the nebulizer 800 is located within the nasal cannula itself, i.e. the aerosol generator is positioned within the nasal cannula 910. During operation of the vibrating mesh 156, the aerosolized particles 220 are fed directly into the stream of breathing gas 915 flowing in the nasal cannula 910. When the outlet 830 of the nebulizer 800 is positioned in line with a nasal prong 920 of the nasal cannula 910, the aerosolized particles 220 are swept into the stream of breathing gas 915 as it turns into the nasal prong 920 for delivery to the patient (see zone C in FIG. 9). In this manner, the nebulized particles 220 do not have sufficient time to impinge the inner walls of the nasal cannula 910, thereby minimizing coalescence of aerosol particles into droplets within the nasal cannula 910 prior to delivery to the patient.

Figure 10:
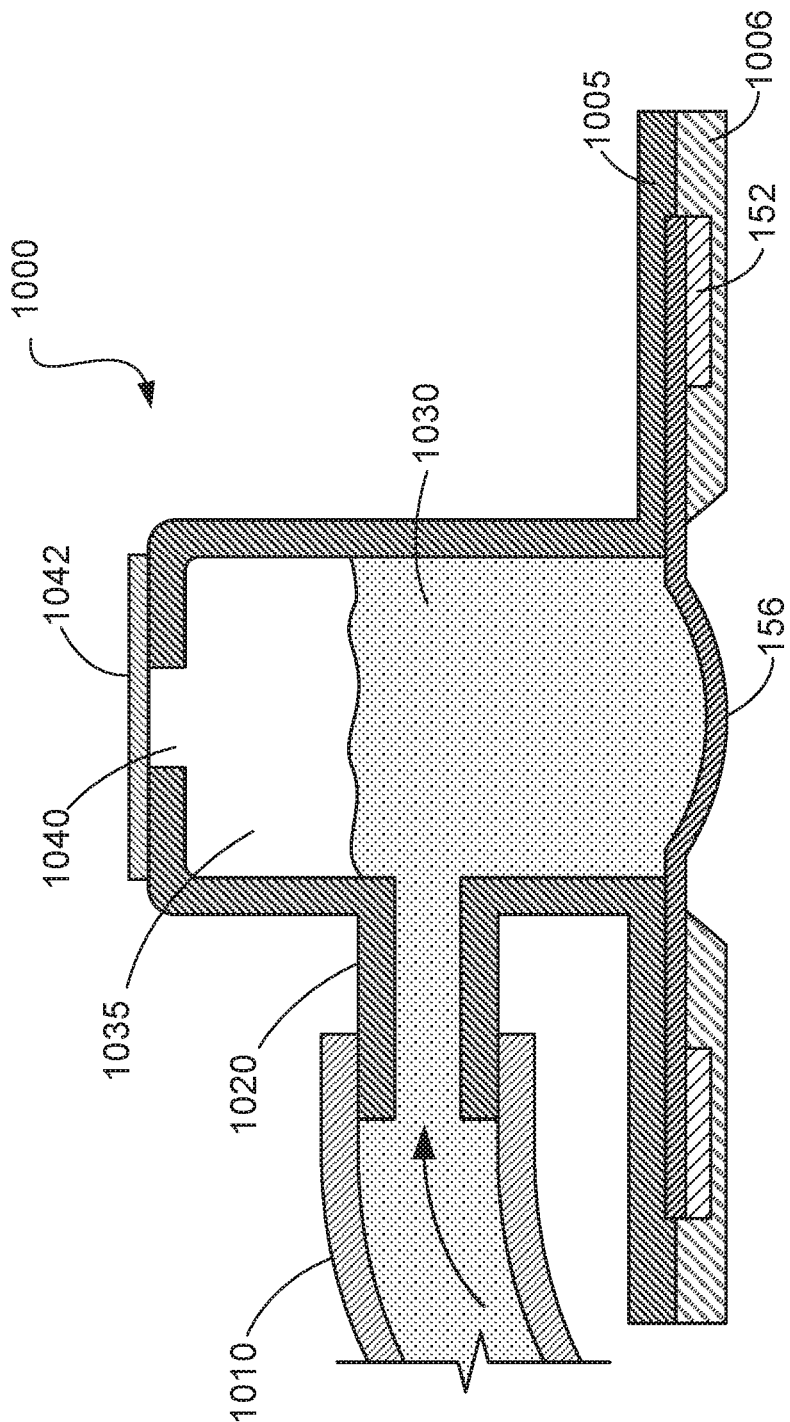
FIG. 10 shows an illustrative cross sectional view of a nebulizer having a small reservoir located on the aerosol generator according to an embodiment of the present disclosure.

FIG. 10 illustrates a nebulizer 1000 having a remote reservoir according to another embodiment of the present disclosure. Nebulizer 1000 is similar to nebulizer 800 in FIG. 8 (where like features have the same labels) except for the presence of a small reservoir of liquid medicament located on the vibrating mesh 156. In this arrangement, the liquid medicament is pumped from the remote reservoir and delivered via feed tube 1010 to the inlet port 1020. The liquid medicament enters the chamber 1030 but does not fill it up completely. Rather, the liquid medicament fills the chamber 1030 to a level above the point at which the inlet port 1020 connects to the chamber 1030. When this happens, the liquid medicament in the chamber 1030 forms a reservoir that is in direct contact with the inner surface 158 of the vibrating mesh 156.

As the liquid medicament does not completely fill the chamber 1030, it forms a free space 1035 between the pressure port 1040 and the surface of the liquid medicament in the chamber 1030. The free space 1035 is exposed to the atmosphere via pressure port 1040, thereby venting the chamber 1030 to the atmosphere. In some implementations, the pressure port 1040 comprises a gas-permeable membrane 1042 that is attached to the opening to the atmosphere. In certain implementations, the gas-permeable membrane 1042 may comprise a Gore-Tex or other Teflon membrane, for example. It should be noted that for venting to be possible, a volume of free space 1035 (i.e. an air gap) between the pressure port 1040 and the surface of the liquid medicament in the chamber 1030 must always be maintained to prevent the buildup of pressure within the chamber 1030. The air gap in free space 1035 is always maintained as long as the flow of liquid medicament into chamber 1030 is less than the rate at which the vibrating mesh 156 converts the liquid medicament to aerosol. The gas-permeable membrane 1042 allows any buildup of pressure in the chamber 1030 to equalize as long as there is air on both sides of the membrane 1042.

Figure 11:
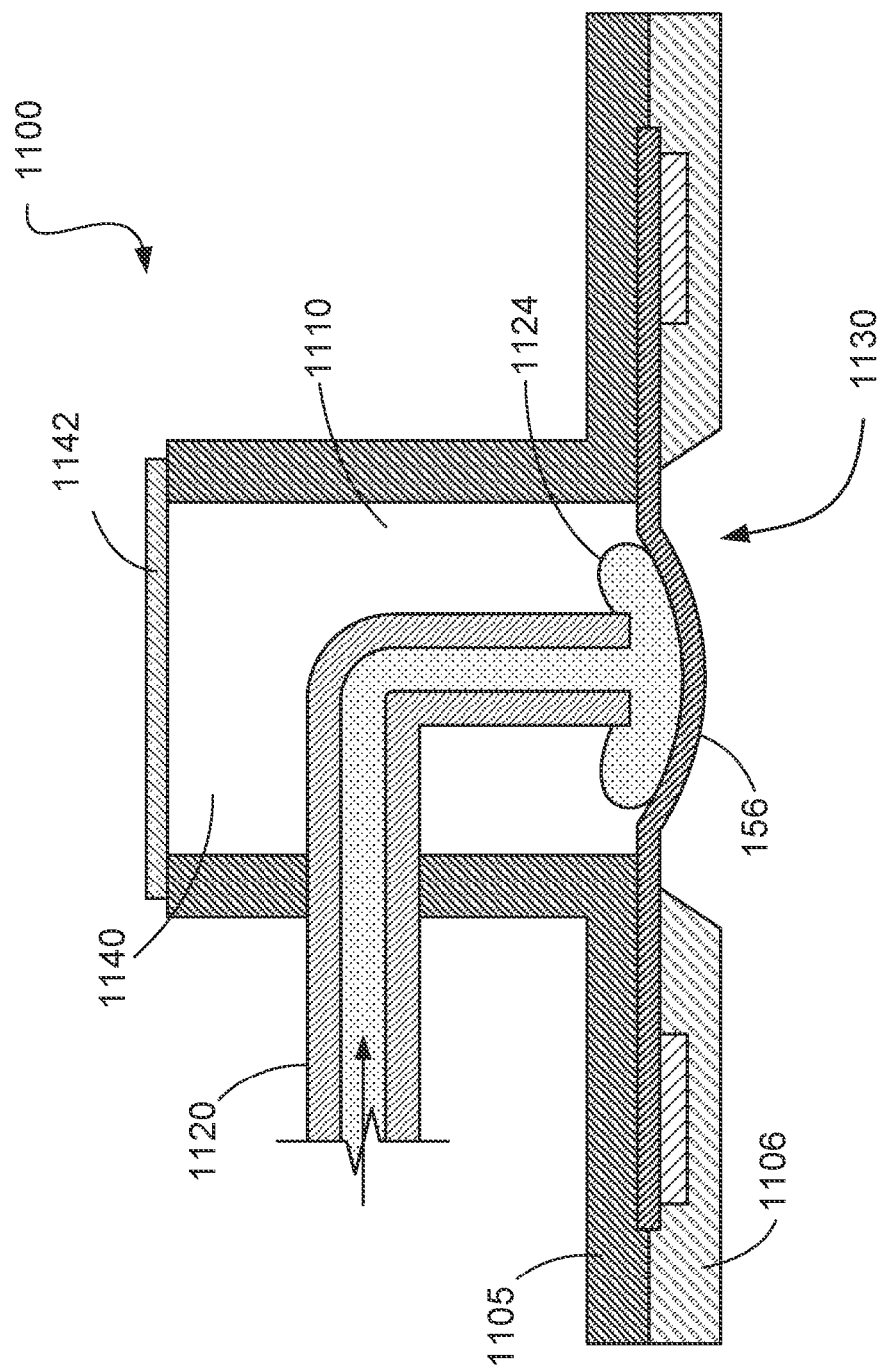
FIG. 11 shows an illustrative cross sectional view of a nebulizer having a drug conduit positioned very close to the mesh of the aerosol generator according to an embodiment of the present disclosure.

FIG. 11 illustrates a nebulizer 1100 having a remote reservoir according to a further embodiment of the present disclosure. Nebulizer 1100 is similar to nebulizer 1000 in FIG. 10 (where like features have the same labels) except that the inlet 1120 in nebulizer 1100 extends into the chamber 1110. Nebulizer 1100 comprises a housing having a first section 1105 and a second section 1106 which may be coupled by any means such as, for example, a magnetic snap fit. The first section 1105 includes a chamber 1110 that is in fluid communication with an inlet 1120, an outlet 1130 and a pressure port 1140. Inlet 1120 defines a drug conduit for the flow of liquid medicament from the remote reservoir for delivery to the nebulizer 1100. A feed tube is connected to the inlet 1120 for the delivery of liquid medicament 154 from a remote reservoir to the chamber 1110 via the drug conduit. The liquid medicament is delivered to the chamber 1110 using a pump (with limited pressure) or gravity feed. A vibrating mesh, such as vibrating mesh 156 in FIG. 2, is positioned at the outlet 1130 for generation of aerosolized particles from the liquid medicament. In the nebulizer 1100, the pressure port 1140 may be covered with a permeable membrane 1142 as described above. In some implementations, the pressure port 1140 may be completely open to the atmosphere.

Unlike the nebulizers described in the foregoing, the inlet 1120 in nebulizer 1100 extends into the chamber 1110 such that the drug conduit is positioned very close to the inner surface 158 of the vibrating mesh 156. For example, the end of the inlet 1120 within chamber 1110 may be positioned within about 2 mm of the inner surface 158 of the mesh 156. Due to the proximity of the end of the inlet 1120 within chamber 1110 and the inner surface 158 of the mesh 156, when a droplet 1124 of liquid medicament is formed against the inner surface of the mesh 156, it is held in place by the surface tension of the liquid medicament.

Figure 12:
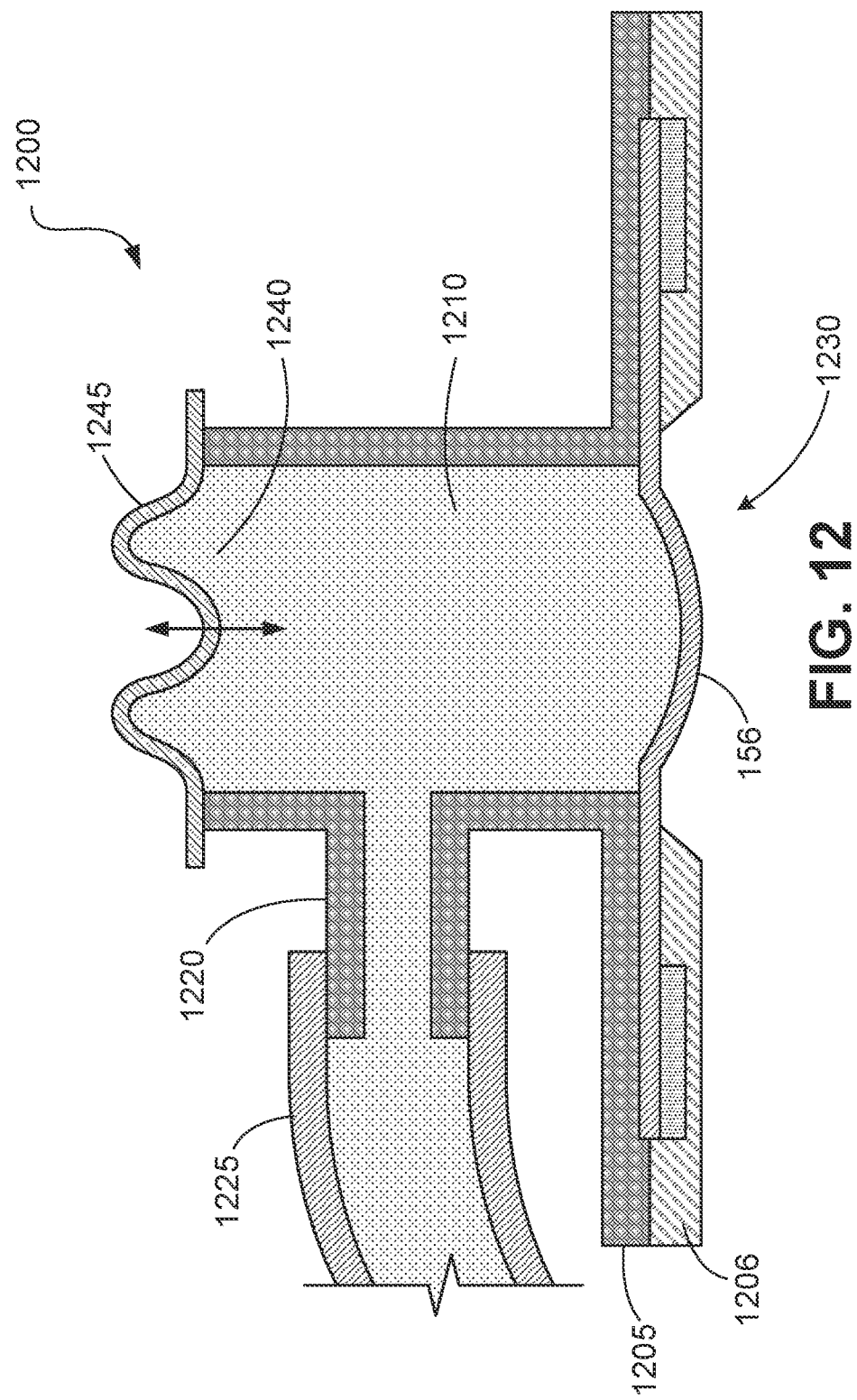
FIG. 12 shows an illustrative cross sectional view of a nebulizer having a small enclosed reservoir with a compliant diaphragm, according to an embodiment of the present disclosure.

FIG. 12 illustrates a nebulizer 1200 having a remote reservoir, such as reservoir 140 in FIG. 1, according to a further embodiment of the present disclosure. Nebulizer 1200 is similar to nebulizer 1000 in FIG. 10 (where like features have the same labels) except for the presence of a compliant diaphragm 1245 instead of the permeable venting membrane attached to the pressure port 1240. Nebulizer 1200 comprises a housing having a first section 1205 and a second section 1206 which may be coupled by any means such as, for example, a magnetic snap fit. The first section 1205 includes a chamber 1210 that is in fluid communication with an inlet 1220, an outlet 1230 and a pressure port 1240. Inlet 1220 defines a drug conduit for the flow of liquid medicament from the remote reservoir for delivery to the nebulizer 1200. A feed tube 1225 is connected to the inlet 1120 for the delivery of liquid medicament from the remote reservoir to the chamber 1210 via the drug conduit. The liquid medicament is delivered to the chamber 1210 using a pump (with limited pressure) or gravity feed. A vibrating mesh, such as vibrating mesh 156 in FIG. 2, is positioned at the outlet 1230 for generation of aerosolized particles from the liquid medicament.

A compliant diaphragm 1245 is attached to the pressure port 1240. The diaphragm 1245 is compliant in that it is able to deform to change the volume of the chamber 1210 so as to equalize the pressure of the chamber 1210 and the pressure of the atmosphere. In certain embodiments the diaphragm 1245 may be permeable to allow any trapped air bubbles in the liquid medicament to escape.

It will be understood that any of the nebulizers in FIGS. 8-12 may be used in any manner so as to provide respiratory therapy to a patient. For example the nebulizers may be positioned such that the vibrating mesh is positioned inside a cannula, as depicted in FIG. 9. In other implementations, the nebulizer may be positioned such that the vibrating mesh is positioned inside a ventilation mask that can be worn by a patient. In another implementation, the nebulizer may be positioned such that the vibrating mesh is positioned alongside a nasal prong of a cannula such that the aerosolized medicament can be entrained into the flow of breathing gas as the breathing gas leaves the nasal prong for inhalation by the patient. In other implementations, the nebulizer may be positioned such that the vibrating mesh is positioned inside a delivery tube connected to a nasal cannula.

The foregoing is merely illustrative of the principles of the disclosure, and the apparatuses can be practiced by other than the described implementations, which are presented for purposes of illustration and not of limitation. It is to be understood that the apparatuses disclosed herein, while shown for use in high flow therapy systems, may be applied to systems to be used in other ventilation circuits.

Variations and modifications will occur to those of skill in the art after reviewing this disclosure. For example, in some embodiments, the conduit may be attached to the outlet opening 360 of the nebulizer 300 to direct the generated aerosol to a desired location (e.g. to the proximal tip of a nasal prong such that a greater proportion of aerosol is entrained in the flow of heat and humidified gas. In certain embodiments, the conduit may be attached to the port 470 in FIG. 4 or the opening 562 in FIG. 5 instead of the opening 360 of the nebulizer 300. In some embodiments, the conduit may be shorter than the length of the nasal prong. As a further example, in certain embodiments, a large antechamber may be formed between the nasal prongs of the cannula into which the aerosol from the nebulizer is provided before entrainment into the flow of heated and humidified gas at the proximal tip of the nasal prongs. Additionally, the permeable membrane attached to the pressure port in FIGS. 8-12 may be replaced with vent holes.

In the foregoing disclosure, it will be understood that the term 'about' should be taken to mean within a range of ±20% of the stated value.

It will be understood that respiratory medications such as bronchodilators, surfactants or antibiotics, may be administered, independently or in combination with each other, through inhalation directly to the patient's lungs using any of the embodiments disclosed in the foregoing. Bronchodilators include, but are not limited to, any medication for treating asthma or Chronic Obstructive Pulmonary Disease ("COPD"), such as Albuterol (Ventolin), Salbutamol (Proventil), and Levosalbutamol/Levalbuterol (Xopenex), for example. Surfactants include, but are not limited to, any medication effective for treating diseases that alter the surface active properties of the lung, such as respiratory distress syndrome in premature infants ("iRDS"), acute respiratory distress syndrome (ARDS), asthma, pneumonia, acute lung injury (ALI), and meconium aspiration syndrome (MAS), for example. Surfactants for inhalation include, but are not limited to, Curosurf (Chiesi Pharmaceuticals), Alveofact (Boehringer Ingelheim), Survanta (Abbott Laboratories), Exosurf (Glaxo Wellcome), and Surfaxin (Discovery Laboratories), for example. Antibiotics include, but are not limited to, any antibiotics suitable for inhalation, such as macrolides (e.g., erythromycin, clarithromycin, azithromycin), glycopeptides (e.g. vancomycin and teicoplanin), oxazoldinone, quinupristin/dalfopristen, aminoglycosides (e.g., gentamicin, tobramycin, amikacin, streptomycin, netilmicin), quinolones (e.g., ciprofloxacin, ofloxacin, levofloxacin), tetracyclines (e.g., oxytetracycline, doxycycline, minocycline), cotrimoxazole, colistin, imepinim, and meripenim, for example. In some embodiments, any medication may be administered through inhalation directly to the patient's lungs using any of the embodiments disclosed in the foregoing.

The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A nebulizer for generating a flow of aerosolized medicament for delivery to a patient, the nebulizer comprising:
   a chamber having an inlet, an outlet in fluid communication with a nasal cannula, and a pressure port;
   a feed tube coupled to the inlet of the chamber for delivery of a liquid medicament from a remote source to the chamber;
   an aerosol generator positioned within the nasal cannula and coupled to the outlet of the chamber and operable to aerosolize the liquid medicament, the aerosol generator having an inner surface in fluidic contact with the liquid medicament, and an outer surface from which the aerosolized medicament is released for delivery to the patient, wherein the outlet of the chamber is positioned in line with at least one nasal prong of the nasal cannula, the nebulizer and the nasal cannula configured to deliver a flow of breathing gas to the patient for inhalation so that the flow of aerosolized medicament is entrained into the flow of breathing gas within the nasal cannula and prior to delivery to the patient via the at least one nasal prong;
   a nozzle within the chamber, the nozzle connected to the inlet and configured such that the liquid medicament is drip fed onto the inner surface of the aerosol generator at atmospheric pressure under the action of gravity; and
   a pressure adjustment element in communication with the pressure port and configured to regulate the pressure within the chamber such that the pressure at the inner and outer surfaces of the aerosol generator is substantially the same.

2. The nebulizer of claim 1, wherein the aerosol generator is a vibrating mesh.

3. The nebulizer of claim 1, wherein the pressure at the inner and outer surfaces of the aerosol generator is maintained at atmospheric pressure.

4. The nebulizer of claim 1, wherein the pressure adjustment element comprises a permeable membrane.

5. The nebulizer of claim 4, wherein the pressure adjustment element additionally comprises a perforated vent.

6. The nebulizer of claim 4, wherein the permeable membrane comprises a Gore-Tex material.

7. The nebulizer of claim 1, wherein the pressure port and outlet are vertically positioned such that the pressure port is located at a topmost section of the chamber, and the outlet is located at the bottommost section of the chamber.

8. The nebulizer of claim 1, wherein the nebulizer further comprises a piezoelectric ring that is connected to the aerosol generator.

9. The nebulizer of claim 8, wherein the aerosol generator is operable to aerosolize the liquid medicament upon receipt of an electric signal via electrical contacts connected to the piezoelectric ring.

10. The nebulizer of claim 1, wherein the nebulizer contains O-rings around the outlet to achieve a liquid tight seal between the chamber and the atmosphere.

11. The nebulizer of claim 1, wherein the liquid medicament comprises at least one of: bronchodilators, surfactants and antibiotics.

12. The nebulizer of claim 1, wherein the medicament comprises at least one of: Albuterol (Ventolin), Salbutamol (Proventil), Levosalbutamol/Levalbuterol (Xopenex), Curosurf (Chiesi Pharmaceuticals), Alveofact (Boehringer Ingelheim), Survanta (Abbott Laboratories), Exosurf (Glaxo Wellcome), Surfaxin (Discovery Laboratories), macrolides, erythromycin, clarithromycin, azithromycin, glycopeptides, vancomycin, teicoplanin, oxazoldinone, quinupristin/dalfopristen, aminoglycosides, gentamicin, tobramycin, amikacin, streptomycin, netilmicin, quinolones, ciprofloxacin, ofloxacin, levofloxacin, tetracyclines, oxytetracycline, doxycycline, minocycline, cotrimoxazole, colistin, imepinim, and meripenim.

13. A system for providing respiratory therapy to a patient, the system comprising:
  a nasal cannula having at least at one nasal prong, tubing configured to receive breathing gas from a breathing gas source, and a breathing gas conduit disposed between the nasal prong and the tubing, the nasal cannula configured to deliver a flow of breathing gas from the at least one nasal prong;
  the nebulizer according to claim 1, operable to generate a flow of aerosolized medicament; and
  a reservoir of liquid medicament located remote from the nebulizer and arranged to supply the nebulizer with the liquid medicament,
  wherein the outlet of the chamber is positioned in line with the at least one nasal prong of the nasal cannula, the nebulizer and the nasal cannula configured to deliver the flow of breathing gas and the flow of aerosolized medicament to the patient for inhalation so that the flow of aerosolized medicament is entrained into the flow of breathing gas within the nasal cannula and prior to delivery to the patient via the at least one nasal prong.

14. The system of claim 13, further comprising a source of breathing gas.

* * * * *